US009757050B2

United States Patent
Ghaffari et al.

(10) Patent No.: US 9,757,050 B2
(45) Date of Patent: Sep. 12, 2017

(54) CATHETER BALLOON EMPLOYING FORCE SENSING ELEMENTS

(71) Applicant: MC10, Inc., Cambridge, MA (US)

(72) Inventors: Roozbeh Ghaffari, Cambridge, MA (US); Yung-Yu Hsu, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 930 days.

(21) Appl. No.: 13/844,767

(22) Filed: Mar. 15, 2013

(65) Prior Publication Data

US 2014/0012160 A1    Jan. 9, 2014

Related U.S. Application Data

(63) Continuation-in-part of application No. 13/568,022, filed on Aug. 6, 2012, and a continuation-in-part of application No. 13/646,613, filed on Oct. 5, 2012.
(Continued)

(51) Int. Cl.
*A61B 5/02* (2006.01)
*A61B 5/05* (2006.01)
(Continued)

(52) U.S. Cl.
CPC .............. *A61B 5/05* (2013.01); *A61B 5/0422* (2013.01); *A61B 5/0538* (2013.01); *A61B 5/6853* (2013.01); *A61B 5/6885* (2013.01); *A61B 5/6858* (2013.01); *A61B 18/1492* (2013.01); *A61B 18/24* (2013.01);
(Continued)

(58) Field of Classification Search
CPC ........ A61B 18/1492; A61B 2018/0022; A61B 2018/00214; A61B 2018/00577; A61B 2018/0016; A61B 5/0422; A61B 18/02; A61B 18/24; A61B 2018/00285;
(Continued)

(56) References Cited

U.S. PATENT DOCUMENTS 3,716,861 A    2/1973 Root
3,805,427 A    4/1974 Epstein
(Continued)

FOREIGN PATENT DOCUMENTS

CN    1864095    11/2006
EP    0585670 A2    3/1994
(Continued)

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
(Continued)

*Primary Examiner* — Joseph Stoklosa
*Assistant Examiner* — Brian M Antiskay
(74) *Attorney, Agent, or Firm* — Nixon Peabody LLP

(57) ABSTRACT

An apparatus for medical diagnosis and/or treatment is provides. The apparatus includes a flexible substrate forming an inflatable body and a plurality of force sensing elements disposed on the flexible substrate. The plurality of force sensing elements are disposed about the inflatable body such that the force sensing elements are disposed at areas of minimal curvature of the inflatable body in a deflated state.

18 Claims, 32 Drawing Sheets

Related U.S. Application Data

(60) Provisional application No. 61/515,713, filed on Aug. 5, 2011, provisional application No. 61/526,516, filed on Aug. 23, 2011, provisional application No. 61/661,221, filed on Jun. 18, 2012, provisional application No. 61/543,713, filed on Oct. 5, 2011, provisional application No. 61/543,748, filed on Oct. 5, 2011.

(51) Int. Cl.
| | |
|---|---|
| *A61B 5/00* | (2006.01) |
| *A61B 5/042* | (2006.01) |
| *A61B 5/053* | (2006.01) |
| A61B 5/04 | (2006.01) |
| A61M 25/10 | (2013.01) |
| A61B 18/14 | (2006.01) |
| A61B 18/24 | (2006.01) |
| A61B 18/00 | (2006.01) |
| A61B 18/02 | (2006.01) |
| A61N 7/00 | (2006.01) |
| A61B 90/00 | (2016.01) |

(52) U.S. Cl.
CPC ............ *A61B 2018/0022* (2013.01); *A61B 2018/00285* (2013.01); *A61B 2018/00345* (2013.01); *A61B 2018/00375* (2013.01); *A61B 2018/00577* (2013.01); *A61B 2018/0212* (2013.01); *A61B 2090/064* (2016.02); *A61B 2090/065* (2016.02); *A61B 2562/046* (2013.01); *A61B 2562/125* (2013.01); *A61B 2562/222* (2013.01); *A61M 25/10187* (2013.11); *A61M 25/10188* (2013.11); *A61M 2025/1093* (2013.01); *A61N 2007/0043* (2013.01); *Y10T 29/49826* (2015.01)

(58) Field of Classification Search
CPC .... A61B 2018/00267; A61B 2018/00797; A61B 2018/1861; A61B 5/0538; A61B 2562/01
USPC ........ 600/372–377, 380–381, 393, 460, 481, 600/508–509; 604/96.01, 97.01, 99.01, 604/103.1; 606/20–32
See application file for complete search history.

(56) References Cited

U.S. PATENT DOCUMENTS

| | | | |
|---|---|---|---|
| 4,058,418 A | 11/1977 | Lindmayer | |
| 4,304,235 A | 12/1981 | Kaufman | |
| 4,416,288 A | 11/1983 | Freeman | |
| 4,658,153 A | 4/1987 | Brosh | |
| 5,306,917 A | 4/1994 | Black | |
| 5,331,966 A | 7/1994 | Bennett | |
| 5,360,987 A | 11/1994 | Shibib | |
| 5,439,575 A | 8/1995 | Thornton et al. | |
| 5,455,430 A | 10/1995 | Noguchi et al. | |
| 5,477,088 A | 12/1995 | Rockett et al. | |
| 5,567,975 A | 10/1996 | Walsh | |
| 5,811,790 A | 9/1998 | Endo | |
| 5,817,008 A | 10/1998 | Rafert et al. | |
| 5,907,477 A | 5/1999 | Tuttle et al. | |
| 6,063,046 A | 5/2000 | Allum | |
| 6,148,127 A | 11/2000 | Adams et al. | |
| 6,421,016 B1 | 7/2002 | Phillips | |
| 6,518,168 B1 | 2/2003 | Clem et al. | |
| 6,567,158 B1 | 5/2003 | Falcial | |
| 6,784,844 B1 | 8/2004 | Boakes et al. | |
| 6,805,809 B2 | 10/2004 | Nuzzo et al. | |
| 6,869,431 B2 * | 3/2005 | Maguire ............... | A61B 18/00 604/103 |
| 6,965,160 B2 | 11/2005 | Cobbley | |
| 6,987,314 B1 | 1/2006 | Yoshida | |
| 7,265,298 B2 | 9/2007 | Maghribi | |
| 7,302,751 B2 | 12/2007 | Hamburgen | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |
| 7,552,031 B2 | 6/2009 | Vock et al. | |
| 7,557,367 B2 | 7/2009 | Rogers | |
| 7,618,260 B2 | 11/2009 | Daniel et al. | |
| 7,622,367 B1 | 11/2009 | Nuzzo | |
| 7,732,012 B2 | 6/2010 | Hongu et al. | |
| 7,759,167 B2 | 7/2010 | Vanfleteren | |
| 7,909,971 B2 | 3/2011 | Nuzzo et al. | |
| 7,960,246 B2 | 6/2011 | Flamand | |
| 7,982,296 B2 | 7/2011 | Nuzzo | |
| 8,008,575 B2 | 8/2011 | De Ceuster et al. | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rodgers | |
| 8,252,191 B2 | 8/2012 | Heejoon et al. | |
| 8,367,035 B2 | 2/2013 | Rogers et al. | |
| 8,372,726 B2 | 2/2013 | De Graff | |
| 8,389,862 B2 | 3/2013 | Arora | |
| 8,394,706 B2 | 3/2013 | Nuzzo et al. | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rodgers | |
| 8,664,699 B2 | 3/2014 | Nuzzo | |
| 8,679,888 B2 | 3/2014 | Rodgers | |
| 8,729,524 B2 | 5/2014 | Rodgers | |
| 8,754,396 B2 | 6/2014 | Rogers | |
| 8,865,489 B2 | 10/2014 | Rodgers | |
| 8,886,334 B2 | 11/2014 | Ghaffari | |
| 8,905,772 B2 | 12/2014 | Rodgers | |
| 8,920,414 B2 * | 12/2014 | Stone ............... | A61B 18/1492 600/372 |
| 9,012,784 B2 | 4/2015 | Arora | |
| 2001/0012918 A1 | 8/2001 | Swanson | |
| 2001/0021867 A1 | 9/2001 | Kordis | |
| 2002/0026127 A1 | 2/2002 | Balbierz | |
| 2002/0082515 A1 | 6/2002 | Campbell | |
| 2002/0094701 A1 | 7/2002 | Biegelsen et al. | |
| 2002/0113739 A1 | 8/2002 | Howard | |
| 2002/0128700 A1 | 9/2002 | Cross, Jr. | |
| 2002/0145467 A1 | 10/2002 | Minch | |
| 2002/0151934 A1 | 10/2002 | Levine | |
| 2003/0017848 A1 | 1/2003 | Engstrom | |
| 2003/0045025 A1 | 3/2003 | Coyle | |
| 2003/0097165 A1 | 5/2003 | Krulevitch et al. | |
| 2003/0120271 A1 | 6/2003 | Burnside et al. | |
| 2003/0162507 A1 | 8/2003 | Vatt | |
| 2003/0214408 A1 | 11/2003 | Grajales | |
| 2003/0236455 A1 | 12/2003 | Swanson | |
| 2004/0006264 A1 | 1/2004 | Mojarradi | |
| 2004/0085469 A1 | 5/2004 | Johnson | |
| 2004/0092806 A1 | 5/2004 | Sagon | |
| 2004/0106334 A1 | 6/2004 | Suzuki | |
| 2004/0135094 A1 | 7/2004 | Niigaki | |
| 2004/0138558 A1 | 7/2004 | Dunki-Jacobs | |
| 2004/0149921 A1 | 8/2004 | Smyk | |
| 2004/0178466 A1 | 9/2004 | Merrill | |
| 2004/0203486 A1 | 10/2004 | Shepherd | |
| 2004/0221370 A1 | 11/2004 | Hannula et al. | |
| 2004/0243204 A1 | 12/2004 | Maghribi et al. | |
| 2005/0021103 A1 | 1/2005 | DiLorenzo | |
| 2005/0067293 A1 | 3/2005 | Naito | |
| 2005/0096513 A1 | 5/2005 | Ozguz | |
| 2005/0107716 A1 | 5/2005 | Eaton | |
| 2005/0113744 A1 | 5/2005 | Donoghue | |
| 2005/0139683 A1 | 6/2005 | Yi | |
| 2005/0171524 A1 | 8/2005 | Stern | |
| 2005/0203366 A1 | 9/2005 | Donoghue | |
| 2006/0003709 A1 | 1/2006 | Wood | |
| 2006/0038182 A1 | 2/2006 | Rodgers | |
| 2006/0068576 A1 | 3/2006 | Burdick, Jr. et al. | |
| 2006/0084394 A1 | 4/2006 | Engstrom | |

(56) References Cited

U.S. PATENT DOCUMENTS

| | | |
|---|---|---|
| 2006/0106321 A1 | 5/2006 | Lewinsky |
| 2006/0128346 A1 | 6/2006 | Yasui |
| 2006/0154398 A1 | 7/2006 | Qing |
| 2006/0160560 A1 | 7/2006 | Josenhans |
| 2006/0264767 A1 | 11/2006 | Shennib |
| 2006/0286785 A1 | 12/2006 | Rogers |
| 2007/0027514 A1 | 2/2007 | Gerber |
| 2007/0108389 A1 | 5/2007 | Makela |
| 2007/0123756 A1 | 5/2007 | Kitajima et al. |
| 2007/0254468 A1 | 11/2007 | Burdick, Jr. et al. |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore et al. |
| 2008/0157235 A1 | 7/2008 | Rodgers |
| 2008/0193749 A1 | 8/2008 | Thompson |
| 2008/0204021 A1 | 8/2008 | Leussler et al. |
| 2008/0211087 A1 | 9/2008 | Mueller-Hipper |
| 2008/0237840 A1 | 10/2008 | Alcoe |
| 2008/0259576 A1 | 10/2008 | Johnson et al. |
| 2008/0287167 A1 | 11/2008 | Caine |
| 2008/0313552 A1 | 12/2008 | Buehler |
| 2009/0000377 A1 | 1/2009 | Shipps et al. |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmyer et al. |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0294803 A1 | 12/2009 | Nuzzo |
| 2009/0308455 A1 | 12/2009 | Kirscht et al. |
| 2009/0322480 A1 | 12/2009 | Benedict et al. |
| 2010/0002402 A1 | 1/2010 | Rodgers |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell et al. |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos et al. |
| 2010/0271191 A1 | 10/2010 | De Graff |
| 2010/0298895 A1 | 11/2010 | Ghaffari et al. |
| 2010/0317132 A1 | 12/2010 | Rodgers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | de Graff |
| 2011/0051384 A1 | 3/2011 | Kriechbaum |
| 2011/0054583 A1 | 3/2011 | Litt |
| 2011/0101789 A1 | 5/2011 | Salter et al. |
| 2011/0121822 A1 | 5/2011 | Parsche |
| 2011/0140897 A1 | 6/2011 | Purks et al. |
| 2011/0175735 A1 | 7/2011 | Forster |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rodgers |
| 2012/0016258 A1 | 1/2012 | Webster et al. |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0083099 A1 | 4/2012 | Nuzzo et al. |
| 2012/0087216 A1 | 4/2012 | Keung et al. |
| 2012/0091594 A1 | 4/2012 | Landesberger |
| 2012/0092178 A1 | 4/2012 | Callsen |
| 2012/0092222 A1 | 4/2012 | Kato et al. |
| 2012/0108012 A1 | 5/2012 | Yasuda |
| 2012/0157804 A1 | 6/2012 | Rodgers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman et al. |
| 2012/0320581 A1 | 12/2012 | Rogers et al. |
| 2012/0327608 A1 | 12/2012 | Rodgers |
| 2013/0036928 A1 | 2/2013 | Rogers et al. |
| 2013/0041235 A1 | 2/2013 | Rodgers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma et al. |
| 2013/0225965 A1 | 8/2013 | Ghaffari |
| 2013/0245388 A1 | 9/2013 | Rafferty et al. |
| 2013/0274562 A1 | 10/2013 | Ghaffari |
| 2013/0313713 A1 | 11/2013 | Arora |
| 2013/0316442 A1 | 11/2013 | Meurville et al. |
| 2013/0316487 A1 | 11/2013 | De Graff |
| 2013/0320503 A1 | 12/2013 | Nuzzo |
| 2013/0321373 A1 | 12/2013 | Yoshizumi |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |

FOREIGN PATENT DOCUMENTS

| | | |
|---|---|---|
| JP | 05-087511 A | 4/1993 |
| JP | 2003297974 | 10/2003 |
| JP | 2009-170173 A | 7/2009 |
| WO | WO 2005/033787 | 4/2005 |
| WO | WO 2005/122285 A2 | 12/2005 |
| WO | WO 2007/003019 A2 | 1/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/002931 | 1/2011 |
| WO | WO 2011/003181 A1 | 1/2011 |
| WO | WO 2011/041727 A1 | 4/2011 |
| WO | WO 2011/084450 A1 | 7/2011 |

(56) References Cited

FOREIGN PATENT DOCUMENTS

| | | |
|---|---|---|
| WO | WO 2011/084709 A2 | 7/2011 |
| WO | WO 2011/127331 A2 | 10/2011 |
| WO | WO 2012/097163 | 7/2012 |
| WO | WO 2012/125494 A2 | 9/2012 |
| WO | WO 2012/158709 | 11/2012 |
| WO | WO 2012/166686 A2 | 12/2012 |
| WO | WO 2012/167096 | 12/2012 |
| WO | WO 2013/010113 | 1/2013 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |

OTHER PUBLICATIONS

Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Ahn, H. et al., "Additive Soft Lithographic Patterning of Submicron and Nanometer-Scale Large Area Resists on Electronic Materials," Nano Letters, 5, 2533-2537 (2005).
Baca, A.J. et al., "Compact monocrystalline silicon solar modules with high voltage outputs and mechanically flexible designs," Energy Environ. Sci., 2010, 3, 208-211.
Baca, A.J. et al., "Printable single-crystal silicon micro/nanoscale ribbons, platelets and bars generated from bulk wafers," Adv. Func. Mater. 17, 3051-3062 (2007).
Bagnall, D.M. et al. "Photovoltaic Technologies," Energy Policy, 2008, 36, 4390.
Bergmann, R.B. "Crystalline Si thin-film solar cells: a review," Appl. Phys. A 69, 187-194 (1999).
Biancardo, M. et al., "Characterization of microspherical semitransparent solar cells and modules," Sol. Energy 81, 711-716 (2007).
Bossert, R.H. et al., "Thin Film Solar Cells: Technology Evaluation and Perspectives," ECN, May 2000.
Brendel, R. "Review of layer transfer processes for crystalline thin-film silicon solar cells," Jpn. J. Appl. Phys. 40, 4431-4439 (2001).
Brendel, R. et al., "Ultrathin crystalline silicon solar cells on glass substrates," Appl. Phys. Lett. 70, 390-392 (1997).
Burgelman, M. et al. "Modeling Thin-Film PV Devices," Progress in Photovoltaics 12, 143-153 (2004).
Cahill, D.G. et al., "Thermal conductivity of epitaxial layers of dilute SiGe alloys," Phys. Rev. B, 71:23, 235202-1-4 (2005).
Campbell, P. et al., "Light Trapping Properties of Pyramidally Textured Surfaces," J. Appl. Phys. 62, 243-249 (1987).
Clugston, D.A. et al., "Modelling Free-Carrier Absorption in Solar Cells," Progress in Phoovoltaics 5, 229-236 (1997).
Clugston, D.A. et al., "PC1D version 5: 32-bit solar cell modeling on personal computers," Photovoltaic Specialist Conference, 1997, Conference Record of the Twenty-Sixth IEEE, 207-210.
Ebong, A. et al., "Rapid Thermal Processing of High Efficiency N-Type Silicon Solar Cells With Al back Junction," 14th World Conference on Photovoltaic Energy Conversion, Hawaii, USA; May 7-12, 2006.
Feng, N.-N. et al., "Design of Highly Efficient Light-Trapping Structures for Thin-Film Crystalline Silocon Solar Cells," IEEE Trans. Elect. Dev. 54, 1926-1933 (2007).
First Office Action dated Mar. 5, 2013 from Chinese Patent Application No. 200980116128.1—includes English translation.
Green, M.A. "Crystalline and thin-film silicon solar cells: state of the art and future potential," Sol. Energy 74, 181-192 (2003).
Heine, C. et al., "Submicrometer Gratings for Solar-Energy Applications," Appl. Opt. 34, 2476-2482 (1995).
International Search Report and Written Opinion, Corresponding to International Application No. PCT/US12/59131, mailed Apr. 8, 2013.
J. Wang et al., "Binding and Diffusion of a Si Adatom Around the Type-A Step on Si(01) c4x2," Appl. Phys. Lett., 66:15, 1954 (1995).
J. Yoon et al., "Arrays of Monocrystalline Silicon Solar Micro-cells for Modules with Ultra-thin, Mechanically Flexible, Semi-transparent and Micro-optic Concentrator Designs," Materials Research Society (MRS) Symposium P: Photovoltaic Materials and Manufacturing Issues, Fall Meeting, Dec. 3, 2008—Abstract provided.
J. Yoon et al., "Ultrathin silicon solar microcells for semitransparent, mechanically flexible and microconcentrator module designs," Nat. Mater., 2008, 7, 907.
Jeon, S. et al., "Fabricating three dimensional nanostructures using two photon lithography in a single exposure step," Optics Express, 14:6, 2300-23208 (2006).
Jeon, S. et al., "Optically fabricated three dimensional nanofluidic mixers for microfluidic systems," Nano Letters, 5:7, 1351-1356 (2005).
K. J. Weber et al., "A Novel Silicon Texturization Method Based on Etching Through a Silicon Nitride Mask," Progress in Photovoltaics: Research and Applications 13, 691-695 (2005).
Kazmerski, L.L. et al., "Solar photovoltaics R&D at the tipping point: A 2005 technology overview." J. Elect. Spec. Rel. Phenom. 150, 105-135 (2006).
Kerschaver, E. V. et al., "Back-contact Solar Cells: A Review," Prog. Photovolt. 14, 107-123 (2006).
Kunnavakkam, M.V. et al., "Low-cost, low-loss microlens arrays fabricated by soft-lithography replication process," Appl. Phys. Lett. 82, 1152-1154 (2003).

(56) References Cited

OTHER PUBLICATIONS

Lee, H.H. et al., "Fabrication of Large Area Stamps, Moulds, and Conformable Photomasks for Soft Lithography," *Journal of Nanoengineering and Nanosystems* 218, 105 (2005).

Lee, K.J. et al., "Bendable GaN High Electron Mobility Transistors on Plastic Substrates," *Journal of Applied Physics* 100, 124507 (2006).

Lei, C. et al., "Grain Boundary Compositions in Cu(InGa)Se$_2$," *J. Appl. Phys.*, 101:2, 24909-1-7 (2007).

Lei, C. et al., "Void formation and surface energies in Cu(InGa)Se$_2$," *J. Appl. Phys.* 100:7, 073518 (2006).

Liao, D. et al., "Cu depletion at the CuInSe$_2$ Surface," *Appl. Phys. Lett.*, 82:17, 2829-2831 (2003).

Liu, Z.X. et al., "A concentrator module of spherical Si solar cell," *Sol. Energy Mater. Sol. Cells* 91, 1805-1810 (2007).

Love, J.C. et al., "Self-Assembled Monolayers of Thiolates on metals as a Form of Nanotechnology," *Chem. Rev.*, 105, 1103-1169 (2005).

M.E. Stewart et al., "Quantitative Multispectral Miosensing and 1-D Imaging Using Quasi-3D Plasmonic Crystals," *Proc. Nat. Acad. Sci.*, 103, 17143-17148 (2006).

Mack, S. et al., "Mechanically flexible thin-film transistors that use ultrathin ribbons of silicon derived from bulk wafers," *Appl. Phys. Lett.*, 88, 213101 (2006).

Malyarchuk, V. et al., "High performance plasmonic crystal sensor formed by soft nanoimprint lithography," *Optics Express*, 13:15, 5669-5675 (2005).

Mercaldo, L.V. et al., Thin film silicon photovoltaics: Architectural perspectives and technological issues, *App. Energy*, 2009, 86, 1836.

Minemoto, T. et al., "Fabrication of spherical silicon crystals by dropping method and their application to solar cells," *Jpn. J. Appl. Phys.* 46, 4016-4020 (2007).

Nelson, B. et al., "Amorphous and Thin-Film Silicon," *NCPV and Solar Program Review*, NREL/CD-520-33586, 583-585, 2003.

Nelson, B. et al., "Project Summary of the NREL Amorphous Silicon Team," *NCPV and Solar Program Review*, NREL/CD-520-33586, 825-828, 2003.

Niggemann, M. et al., Realization of Ultrahigh Photovoltaics with Organic Photovoltaic Nanomodules, *Adv. Mater.* 2008, 20, 4055.

Notice of Allowance corresponding to Korean Patent Application No. 10-20102-7010094, dated Feb. 25, 2013—includes English translation.

Notice of Allowance, U.S. Appl. No. 12/398,811 mailed May 24, 2013.

Notice of Final Rejection for Japanese Patent Application No. 2006-16159, dated Apr. 16, 2013.

Notice of Preliminary Rejection corresponding to Korean Patent Application No. 10-2007-7000216, dated Feb. 21, 2013—includes English translation.

Notice of Preliminary Rejection corresponding to Korean Patent Application No. 10-2012-7030789, dated Feb. 25, 2013—includes English translation.

Office Action, Corresponding to Chinese Patent Application No. 200980116280.1, mailed Mar. 5, 2013.

Office Action, Corresponding to U.S. Appl. No. 13/441,618, mailed May 23, 2013.

Office Action, Corresponding to U.S. Appl. No. 13/120,486, mailed Apr. 12, 2013.

Orega, P. et al., "High Voltage Photovoltaic Mini-modules," *Progr. Photovolt.: Res. Appl.*, 2008, 16, 369.

Pizzini, S., "Bulk solar grade silicon: how chemistry and physics play to get a benevolent microstructured material," *Appl. Phys. A: Mater. Sci. Process.*, 2009, 96, 171.

R. Rockett et al., "Prediction of dopant ionization energies in silicon: The importance of strain," *Physical Review B*, 6823:23, 3208 (2003).

Rockett, A. "The effect of Na in polycrystalline and single crystal CuIn$_{1-x}$Ga$_x$Se$_2$," *Thin Solid Films*, 480-1, 2-7 (2005).

Rockett, A. et al., "A Monte Carlo simulation of the growth of si(001)2x1: adatom/SA step interactions and growth mechanisms," *Surf. Sci.*, 312, 201 (1994).

Rockett, A. et al., "Near-surface Defect Distributions in Cu(In,Ga)Se$_2$," *Thin Solid Films*, 431-2, 301-306 (2003).

Roedern, B. "Status of Amorphous and Crystalline Thin-Film Silicon Solar Cell Activities," *NCPV and Solar Program Review*, NREL/CD-520-33586, 552-555, 2003.

Ruby, D.S. et al., "Rie-texturing of multicrystalline silicon solar cells," *Solar Energy Materials & Solar Cells* 74, 133-137 (2002).

Sha, A. et al., "Recent progress on microcrystalline solar cells.," *Photovoltaic Specialists Conference, Conference Record of the Twenty-Sixth IEEE*, 569-574 1997).

Sinton, R.A. et al., "27.5-Percent Silicon Concentrator Solar-Cells," *IEEE Elect. Dev. Lett.* 7, 567-569 (1986).

Sobajima et al., "Microstructures of high-growth-rate (up to 8.3 nm/s) microcrystalline silicon photovoltaic layers and their influence on the photovoltaic performance of thin-film solar cells," *J. Non-Cryst. Solids*, 2008, 354, 2407.

Sun, Y. et al., "Gigahertz Operation in Mechanically Flexible Transistors on Plastic Substrates," *Applied Physics Letters* 88, 183509 (2006).

Sun, Y. et al., "Printed Arrays of Aligned GaAs Wires for Flexible Transistors, Diodes and Circuits on Plastic Substrates," *Small* 2(11), 1330-1334 (2006).

Sun, Y. et al., "Top Down Fabrication of Semiconductor Nanowires With Alternating Structures Along Their Transverse and Longitudinal Axes," *Small* 1(11), 1052-1057 (2005).

Taguchi, M. et al., "HIT™ cells—High efficiency crystalline Si cells with novel structure," *Prog. Photovolt.* 8, 503-513 (2000).

Verlinden, P.J. et al., "Silver (R) solar cells: A new thin-crystalline silicon photovoltaic technology," *Sol. Energy Mater. Sol. Cells* 90, 3422-3430 (2006).

Weber, K.J. et al., "A Novel-Low Cost, High Efficiency Micromachined Silicon Solar Cell," *IEEE Electron Device Letters*, vol. 25, No. 1, 37-39 (2004).

Wenham, S.R. et al., "Buried contact silicon solar cells," *Solar Energy Materials and Solar Cells*, 34, 101-110 (1994).

Yamamoto, K. et al., "Thin-film poly-Si solar cells on glass substrate fabricated at low temperature," *Applied Physics A: Materials Science & Processing* 69, 179-185 (1999).

Zhao et al., "24.5% efficiency silicon PERT cells on MCZ substrates and 24.7% efficiency PERL cells on FZ substrates," *Prog. Photovolt.* 7, 471-474 (1999).

International Search Report for PCT/US12/59131, dated Apr. 8, 2013, 6 pages.

\* cited by examiner

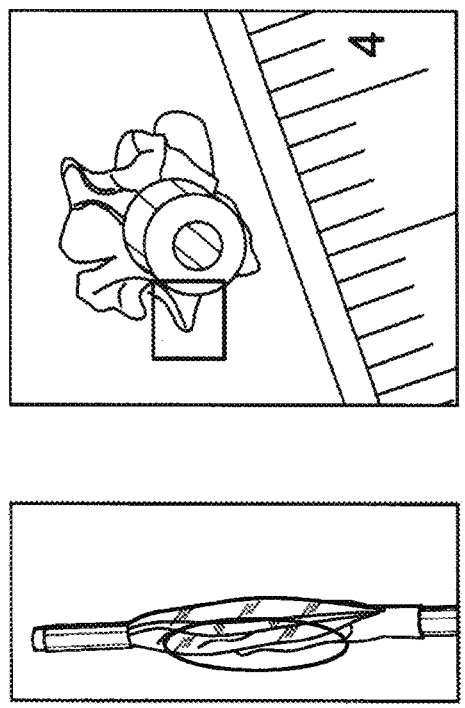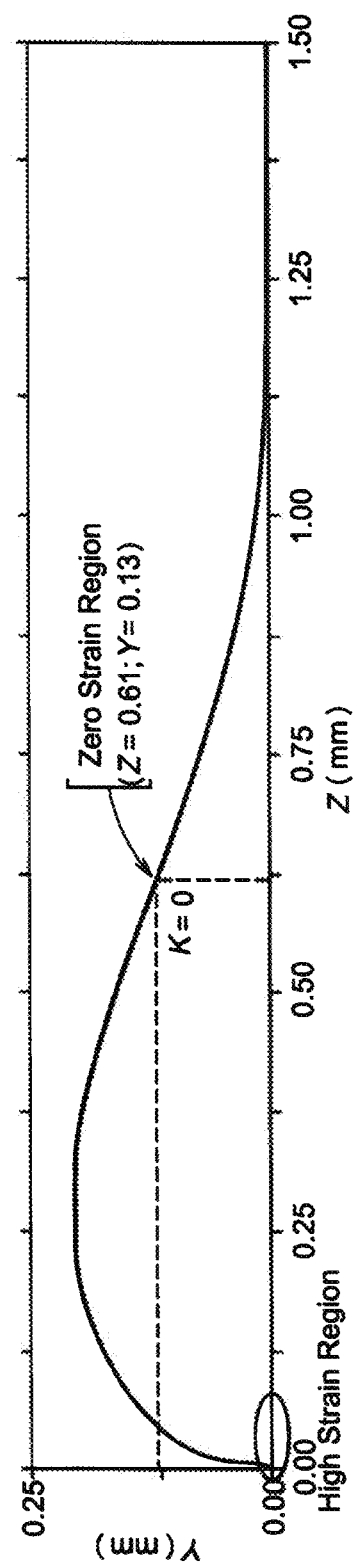
FIG. 9

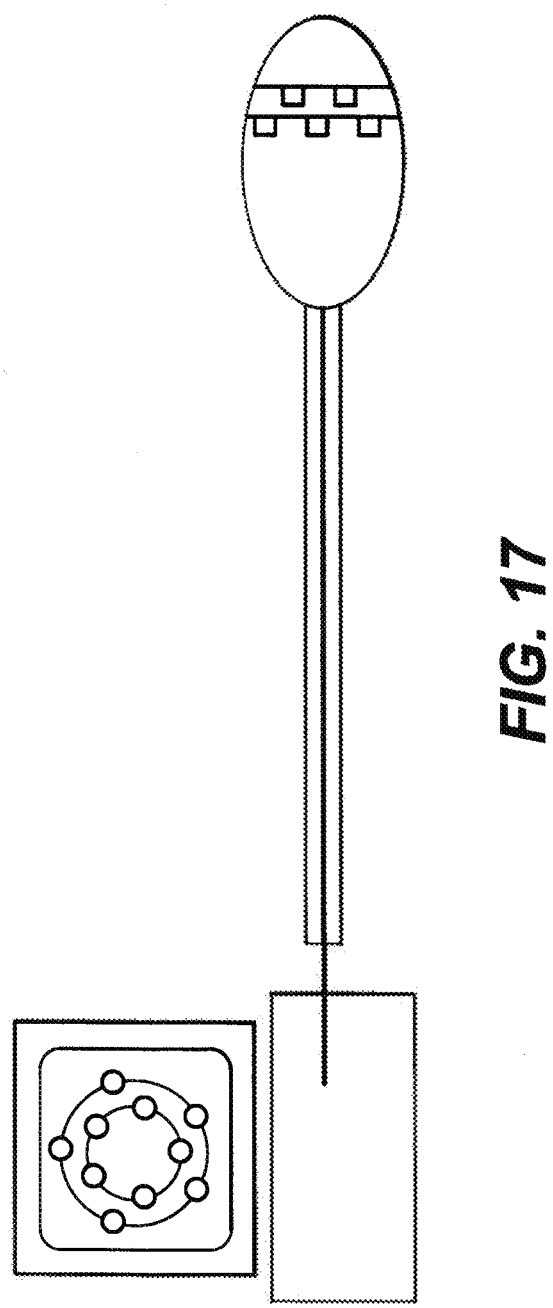

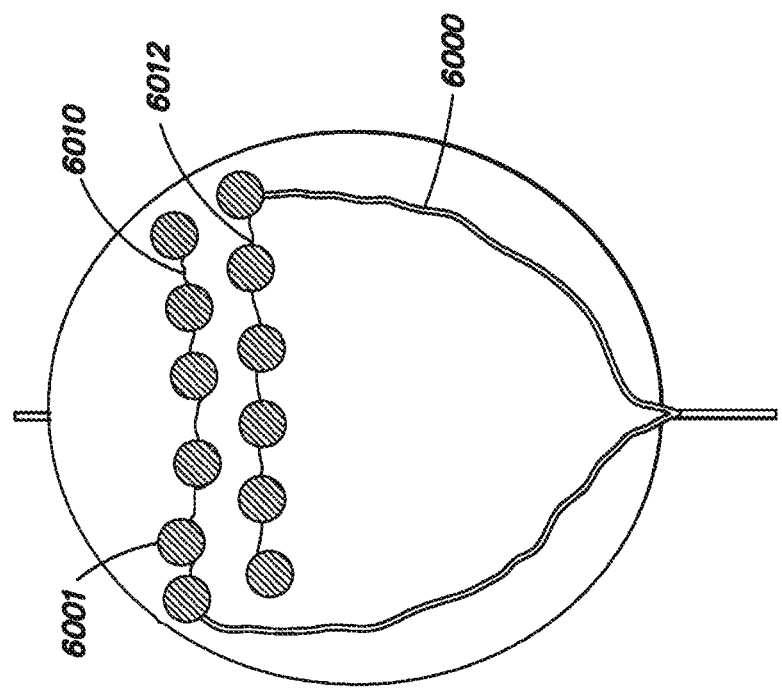
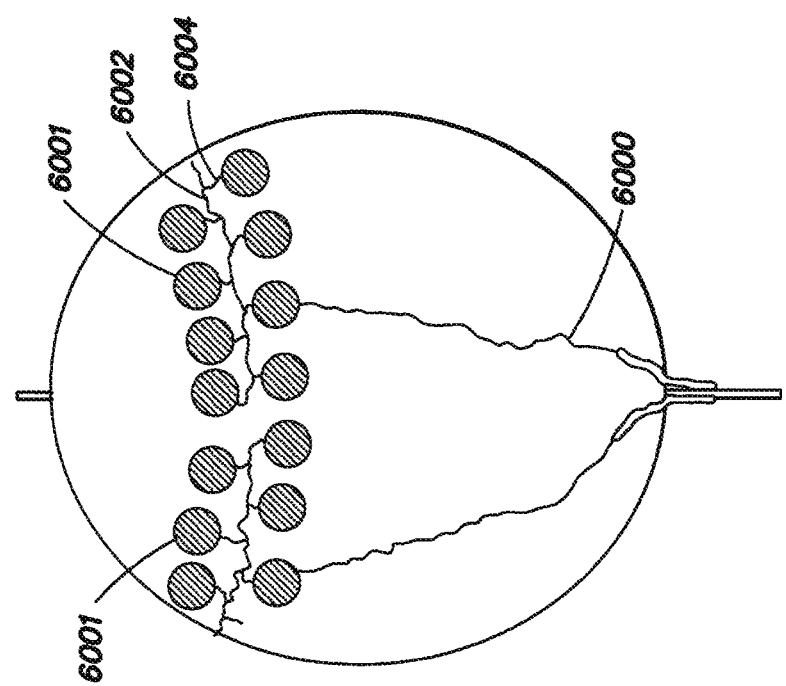

CATHETER BALLOON EMPLOYING FORCE SENSING ELEMENTS

CROSS-REFERENCES TO RELATED APPLICATIONS

This application claims priority to U.S. Non-provisional application Ser. No. 13/568,022, filed on Aug. 6, 2012 entitled "Catheter Balloon Methods and Apparatus Employing Sensing Elements," which claims priority to and benefit of U.S. Provisional Application No. 61/515,713, filed on Aug. 5, 2011, U.S. Provisional Application No. 61/526,516, filed on Aug. 23, 2011, and U.S. Provisional Application No. 61/661,221, filed on Jun. 18, 2012." The entire disclosure of each of these applications is incorporated herein by reference in its entirety, including drawings.

This application also claims priority to U.S. Non-provisional application Ser. No. 13/646,613, filed on Oct. 5, 2012, entitled "Cardiac Catheter Employing Conformal Electronics For Mapping," which claims priority to and benefit of U.S. Provisional Application No. 61/543,713, filed on Oct. 5, 2011, and U.S. Provisional Application No. 61/543,748, filed on Oct. 5, 2011. The entire disclosure of each of these applications is incorporated herein by reference in its entirety, including drawings.

BACKGROUND

High quality medical sensing and imaging data has become increasingly beneficial in the diagnoses and treatment of a variety of medical conditions. The conditions can be associated with the digestive system, the cardio-circulatory system, and can include injuries to the nervous system, cancer, and the like. For example, complex fractionated electrogram (CFAE) triggers within the right and left atria play a role in the pathogenesis of persistent and permanent atrial fibrillation, atrial flutters, and tachycardias. Radio frequency (RF) energy can be used to ablate tissues to correct aberrant conduction pathways, aided by imaging data.

SUMMARY

The Inventors have recognized and appreciated that inflatable bodies that include sensing elements can provide data measurements that could beneficial medical diagnosis and/or treatment. The inventors have also recognized that such systems can be made more robust to the use in medical diagnosis and/or treatment environment, provide useful measurements of tissue states (including amount of contact with the tissue), and maintain optimal performance, if the force sensing elements are selectively disposed at certain regions of the inflatable body. In view of the foregoing, various embodiments herein are directed generally to methods, apparatus and systems for medical diagnosis and/or treatment that include a flexible substrate forming an inflatable body and a plurality of sensing elements disposed on the flexible substrate, where the force sensing elements are selectively disposed at certain regions of the inflatable body.

In some examples herein, an apparatus is provided for medical diagnosis and/or treatment that includes a flexible substrate forming an inflatable body and a plurality of force sensing elements disposed on the flexible substrate. Each of the plurality of force sensing elements detects data indicative of a degree of contact between of a portion of the inflatable body and a surface.

According to the principles disclosed herein, an apparatus for medical diagnosis and/or treatment can include a flexible substrate forming an inflatable body and a plurality of force sensing elements disposed on the flexible substrate. Each force sensing element of the plurality of force sensing elements can also include two conductive components, disposed substantially parallel to each other and an elastic dielectric component disposed between the two conductive components, wherein a measure of an electrical property of at least one of the conductive components provides an indication of a force applied to the inflatable body.

In an example, the apparatus can also include a flexible substrate forming an inflatable body, and a coupling bus disposed on the flexible substrate about a portion of a circumference of the inflatable body. The force sensing elements can include two conductive components, disposed substantially parallel to each other, and an elastic dielectric component disposed between the two conductive components. Each of the force sensing elements can be coupled to the coupling bus and measure an the electrical properties of the conductive components can provide an indication of a force applied to the inflatable body.

In an example, the coupling bus can be a serpentine bus. The serpentine bus can electrically couple at least one conductive component of each of the plurality of force sensing elements. In an example, an encapsulation material can be disposed over a portion of the coupling bus. The encapsulation material can include polyurethane.

In an example, the shaft can be coupled to the inflatable body, can the shaft can include a cryoablation device, a laser ablation device, a high intensity ultrasound or a RF device.

In an example, the coupling bus can be an annular bus, and the annular bus can be disposed as a ring substantially about a circumference of the inflatable body. In another example, the coupling bus can be a serpentine bus and can include a plurality of serpentine structures.

In an example, the force sensing elements can be disposed about an equator of the inflatable body. The force sensing elements can be disposed proximate to a distal portion of the inflatable body. In another example, the plurality of force sensing elements can be disposed in helical a pattern about the inflatable body. The inflatable body can be disposed near a distal end of a catheter.

In an example, the inflatable body can be a balloon. The balloon can be cylindrical, onion-shaped, cone-shaped, dog-bone-shaped, barrel-shaped.

In an example, the coupling bus can have a T-configuration or an annular ring structure.

In an example, the force applied to the inflatable body can cause a degree of compression of the elastic dielectric component between the two conductive components, and the measure of the electrical property of the conductive components changes based on the degree of compression of the elastic dielectric component, thereby providing an indication of the force applied to the inflatable body.

In an example, the force sensing elements can be formed from a conductive material. One of the two conductive components of the force sensing element can be larger than another of the two conductive components.

According to the principles disclosed herein, a method of fabricating an apparatus for medical diagnosis and/or treatment can include providing a coupling bus that can be coupled to a plurality of force sensing elements. Each of the force sensing elements of the plurality of force sensing elements can include two conductive components, disposed substantially parallel to each other. The force sensing elements can also include an elastic dielectric component disposed between the two conductive components. The method can further include disposing the coupling bus about a region of an inflatable body and disposing the plurality of force sensing elements about a portion of a circumference of the inflatable body.

In an example, the method can further include extracting the coupling bus and the plurality of force sensing elements from a carrier substrate prior to disposing the coupling bus about the region of the inflatable body.

In an example, each of the force sensing elements can include a respective first conductive component and a respective second conductive component. In another example, disposing the coupling bus about the region of the inflatable body can include applying the respective first conductive component of each of the plurality of force sensing elements to a portion of flexible substrate bus, and disposing the respective second conductive component substantially parallel to the respective first conductive component of each of the plurality of force sensing elements.

According to the principles disclosed herein, method of performing a medical diagnosis and/or treatment on a tissue can include disposing in proximity to the tissue an apparatus. The apparatus can include a flexible substrate forming an inflatable body. The apparatus can also include a coupling bus, and a plurality of force sensing elements that can be coupled to the coupling bus. Each of the force sensing elements of the plurality of force sensing elements can include two conductive components, disposed substantially parallel to each other, and an elastic dielectric component disposed between the two conductive components. The method can also include recording an electrical measurement of at least one force sensing element of the plurality of force sensing elements. The measurement can provide an indication of a force applied to the inflatable body.

In an example, the measurement provides an indication of a contact state of the portion of the tissue with the at least one force sensing element of the plurality of force sensing elements.

According to the principles disclosed herein, an apparatus for displaying a representation of measurements of a plurality of force sensing elements disposed about at least a portion of a circumference of an inflatable body during a medical diagnosis and/or treatment of a tissue can include a display, memory storing processor-executable instructions, and one or more processor units to execute the processor-executable instructions. The execution of the processor-executable instructions can cause the display to display a plurality of representations of the measurements. Each representation of the plurality of representations can correspond to a force sensing element of the plurality of force sensing elements. Each force sensing element of the plurality of force sensing elements can include two conductive components, disposed substantially parallel to each other and an elastic dielectric component disposed between the two conductive components.

In an example, the representation can include a plurality of first indicators, each first indicator corresponding to a force sensing element of the plurality of force sensing elements that measures a force below a threshold value, and a plurality of second indicators, each second indicator corresponding to a force sensing element of the plurality of force sensing elements that measures a force above the threshold value.

In an examples, the measurement below the threshold value indicates that the corresponding force sensing element of the plurality of force sensing elements may not in contact with the tissue, and the measurement above the threshold value indicates that at least a portion of the corresponding force sensing element of the plurality of force sensing elements can be in contact with the tissue.

According to the principles disclosed herein, a system for mapping contact with a surface can include an inflatable body and a plurality of force sensing elements coupled to the inflatable body. Each of the force sensing elements can include two conductive components, disposed substantially parallel to each other and an elastic dielectric component disposed between the two conductive components. The system can also include an electronic display electrically coupled to the plurality of force sensing elements, the electronic display providing a visual representation of the spatial location of each of the plurality of force sensing elements on the inflatable body. The electronic display can change a visual attribute of the visual representation of a respective force sensing element in response to a change in an electrical measurement of the respective force sensing element. A change in the electrical measurement can identify a contact condition of the respective force sensing element with respect to the surface.

In an example, the visual attribute can be a binary representation and/or a quantitative representation.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS."

Kim, D. H. et al. (2010). Dissolvable films of silk fibroin for ultrathin conformal bio-integrated electronics. *Nature Materials*, 9, 511-517.

Omenetto, F. G. and D. L. Kaplan. (2008). A new route for silk. *Nature Photonics*, 2, 641-643.

Omenetto, F. G., Kaplan, D. L. (2010). New opportunities for an ancient material. *Science*, 329, 528-531.

Halsed, W. S. (1913). Ligature and suture material. *Journal of the American Medical Association*, 60, 1119-1126.

Masuhiro, T., Yoko, G., Masaobu, N., et al. (1994). Structural changes of silk fibroin membranes induced by immersion in methanol aqueous solutions. *Journal of Polymer Science*, 5, 961-968.

Lawrence, B. D., Cronin-Golomb, M., Georgakoudi, I., et al. (2008). Bioactive silk protein biomaterial systems for optical devices. *Biomacromolecules*, 9, 1214-1220.

Demura, M., Asakura, T. (1989). Immobilization of glucose oxidase with *Bombyx mori* silk fibroin by only stretching treatment and its application to glucose sensor. *Biotechnololgy and Bioengineering*, 33, 598-603.

Wang, X., Zhang, X., Castellot, J. et al. (2008). Controlled release from multilayer silk biomaterial coatings to modulate vascular cell responses. *Biomaterials*, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

Further combinations and sub-combinations of various concepts are provided below in the claims section. It should be appreciated that all combinations of such concepts and additional concepts described in greater detail below (provided such concepts are not mutually inconsistent) are contemplated as being part of the inventive subject matter disclosed herein. In particular, all combinations of subject matter appearing as numbered claims at the end of this disclosure are contemplated as being part of the inventive subject matter disclosed herein. In addition, all combinations of subject matter supported by this disclosure, including the drawings, the description and the claims, are contemplated as being part of the inventive subject matter even if not expressly recited as one of the numbered claims.

It should be appreciated that all combinations of the foregoing concepts and additional concepts described in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 9 is a graph illustrating example computation of the change in strain along a folded section of a deflated balloon, according to the principles described herein.

FIG. 17 shows a schematic example of a balloon catheter including integrating sensing elements coupled with a data acquisition and graphical user interface, according to the principles described herein.

FIGS. 26A-26B illustrates further additional examples of the sensor array, including "L" shaped arrays, according to the principles described herein.

Figure 1A:
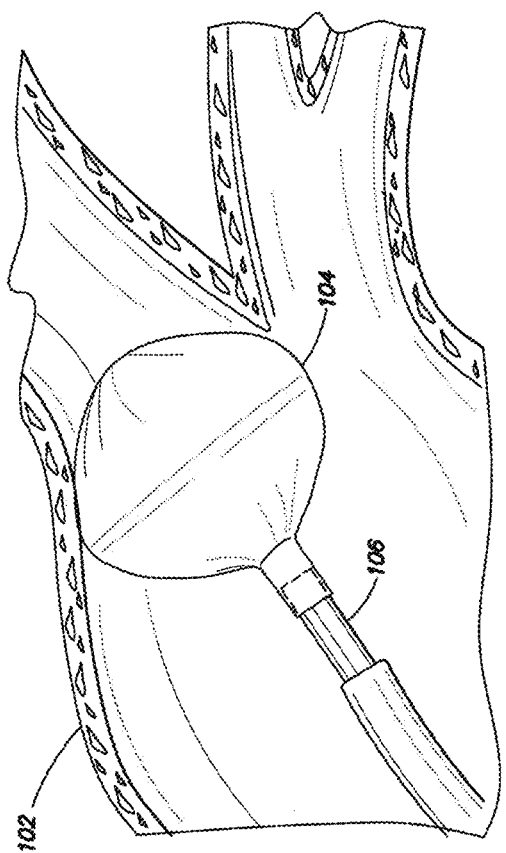
FIG. 1A illustrates an example illustration of an incomplete occlusion of the ostium or pulmonary vein by a catheter balloon, where a dye is deployed to help visualization of the incomplete occlusion according to the principles described herein.

The features and advantages of the various examples will become more apparent from the detailed description set forth below when taken in conjunction with the drawings.

DETAILED DESCRIPTION

Following below are more detailed descriptions of various concepts related to, and examples of inventive systems, methods and apparatus for use with balloon catheters and other types of catheters. The systems, methods and apparatus used for medical diagnosis and/or treatment. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but not limited to, the term "including" means including but not limited to. The term "based on" means based at least in part on.

An example system, method and apparatus described herein can be used for medical diagnosis and/or treatment. The apparatus can include a substrate forming an inflatable body and a plurality of force sensing elements disposed on the flexible substrate. Each of the force sensing elements of the plurality of force sensing elements can include at least two conductive components. The at least two conductive components can be disposed substantially parallel to each other. The force sensing elements also include an elastic dielectric component disposed between the at least two conductive components. In the apparatus, a measure of an electrical property of at least one of the conductive components provides an indication of a force applied to the inflatable body. The indication of the force can be used to provide an indication of the degree or the state of contact of a force sensing element with a surface.

An example apparatus for medical diagnosis and/or treatment according to the principles herein can also include a flexible substrate forming an inflatable body and a coupling bus disposed on the flexible substrate about a portion of a circumference of the inflatable body. Each of the force sensing elements can include two conductive components, disposed substantially parallel to each other and an elastic dielectric component disposed between the two conductive components. A measure of an electrical property of at least one of the conductive components provides an indication of a force applied to the inflatable body.

According to the principles disclosed herein, an example method for fabricating an apparatus for medical diagnosis and/or treatment includes providing a coupling bus that is coupled to a plurality of force sensing elements. The force sensing elements can include two conductive components, disposed substantially parallel to each other and an elastic dielectric component disposed between the two conductive components. In this example, the method can also include disposing the coupling bus about a region of an inflatable body and disposing the force sensing elements about a portion of a circumference of the inflatable body.

An example method for performing medical diagnosis and/or treatment on a tissue according to the principles herein includes disposing an apparatus in the proximity of the tissue. The apparatus can include a flexible substrate forming an inflatable body, a coupling bus, and a plurality of force sensing elements that are coupled to the coupling bus. Each of the force sensing elements can include two conductive components disposed substantially parallel to each other and an elastic dielectric component disposed between the two conductive components. In this example, the method also can include recording an electrical measurement of at least one force sensing element of the plurality of force sensing elements. The data from the measurement can be used to provide an indication of a force applied to the inflatable body.

An example apparatus for displaying a representation of measurements of a plurality of force sensing elements disposed on an inflatable body according to the principles herein includes a display, a memory storing processor-executing instructions, and one or more processors units to executed the processor-executing instructions. The processor-executing instructions cause the display to display a plurality of representations of the measurements and each representation of the plurality of representations corresponds to a force sensing element of the plurality of force sending elements. The force sensing elements can include two conductive components disposed substantially parallel to each other and an elastic dielectric component disposed between the two conductive components.

An example system for mapping contact with a surface according to the principles herein includes an inflatable body, a plurality of force sensing elements coupled to the inflatable body, and an electronic display. The force sensing elements can include two conductive components disposed substantially parallel to each other and an elastic dielectric component disposed between the two conductive components. The electronic display can provide a visual representation of the spatial location of each of the plurality of force sensing elements on the inflatable body. In this example, the electronic display changes a visual attribute of the visual representation of a respective force sensing element in response to a change in an electrical measurement of the respective force sensing element. The change in the electrical measurement can identify a contact condition of the respective force sensing element with respect to the surface.

FIG. 1A illustrates an example of an example system or apparatus according to the principles described herein, disposed against a surface. In this example, the example system or apparatus can be used for an incomplete occlusion of the tissue lumen 102 (e.g., ostium, pulmonary vein, or renal artery) by an inflatable body (here it is catheter balloon 104) positioned near a distal end of a catheter, according to the principles described herein. The example catheter balloon 104 shown in FIG. 1A is depicted as having an "onion" shape described herein. The example catheter of FIG. 1A includes a shaft 106. In an example, an ablative therapy can be introduced through shaft 106. According to the principles herein, the plurality of sensing elements, the coupling bus, and/or the stretchable electronic system that includes the flexible annular interconnect and the plurality of sensing elements can be disposed about the catheter balloon 104.

The plurality of sensing elements described herein can be formed as sets of nanomembrane sensors and conformal electronics that can be used to perform a medical diagnosis and/or treatment as described herein. That is, the plurality of sensing elements described herein can be disposed on the inflatable body (here catheter balloon 104 of FIG. 1) without substantially changing the mechanics and/or thermal profiles of the inflatable body.

In an example, the fabrication and implementation of highly conformal arrays of capacitive-based force sensing elements on balloon catheters are described herein. Various examples of the systems herein include arrays of sensing elements that are configured in a circumferential orientation on the balloon surface. In another example, the sensing elements can be configured in a linear orientation along one of the longitudinal axes of the balloon surface. The use of sensor arrays on an inflatable body as described herein can be used to provide an insight into localized mechanical interactions of the inflatable body and tissue, which can be poorly visualized with point sensing techniques. An example system according to the principles herein can provide for high sensitivity contact sensing. An example system according to the principles herein also can be used to provide insight into, e.g., occlusion, thermal interactions, and gap localization on the inflatable body (e.g., a cryoballoon).

An example force sensing element that measures contact force of a catheter with internal lumen vein or arterial surfaces can be introduced into a lumen prior to and following occlusion. Changes in pressure caused by occlusion can be assessed. This approach may facilitate assessing localized activity at different quadrants of the inflatable body (e.g., the catheter balloon) that align with the anatomy of the lumen.

The systems, methods and apparatus described herein provide design strategies and fabrication techniques to achieve high performance stretchable electronics systems that are also flexible and that can be seamlessly integrated with inflatable bodies. The stretchable electronics systems can include the plurality of sensing elements, the coupling bus, and/or the flexible annular interconnect including the plurality of sensing elements. The stretchable electronics systems can be fabricated using inorganic semiconductor processes.

In an example, the force sensing elements, the coupling bus, and/or the stretchable electronic system that includes the flexible annular interconnect and the plurality of force sensing elements may be fabricated on a rigid and/or brittle substrate and then applied to the surface of the inflatable body. That is, various forms of high performance electronics may be fabricated on the rigid and brittle surfaces of semiconductor wafers or metallic wires in formats that are inherently low density may be incompatible with establishing intimate physical coupling with the complex topologies of the atria and ventricles due to their rigidity. Various electronic systems may be further limited by their inability to offer simple modes of functionality that do not allow real-time mapping over multiple sensor nodes. The systems, methods and apparatus described herein provide technology to integrate thin, conformal arrays of force sensing elements on inflatable bodies, including deformable substrates such as silicone or polyurethane balloon skins. The integrated systems and apparatus described herein permit electrical, thermal, and chemical sensing components to be implemented on the surface of inflatable bodies.

In an example, the force sensing elements, the coupling bus, and/or the stretchable electronic system that includes the flexible annular interconnect and the plurality of force sensing elements can be formed using the ultrathin designs of inorganic nanomaterials. These ultrathin designs permit implementation of flexible electronics over very small bending radii, for example less than 100 microns. However, extreme bending and stretching conditions may induce greater strains or fractures in a material, such as in instances where these electronics interface with soft tissue lumen (including soft tissues of the heart). For example, electronics on the heart can undergo large strains up to 10-20% or more. Sensors on inflatable bodies for minimally invasive procedures may be subjected to even higher mechanical strain, exceeding 100% strains in some instances. To alleviate the strains induced in these situations, various forms of flexible nanomaterials may be implemented, and may include serpentine layouts or buckled structures.

Stretchability of over 200% of the stretchable electronics systems may be accomplished with non-coplanar serpentine-shaped interconnects. Device islands or sensing elements may be coupled to a flexible substrate of an inflatable body via covalent bonding. Serpentine interconnects may be loosely coupled through van der Waals forces. Therefore, subjecting the substrate to deformation may cause the metal interconnects, such as but not limited to the serpentine interconnects, to detach from the underlying substrate thereby relieving stress from the device islands. As a result, the maximum principal strain exerted on the interconnects can be reduced by two orders of magnitude compared to the strain applied to the underlying substrate.

Figure 1B:
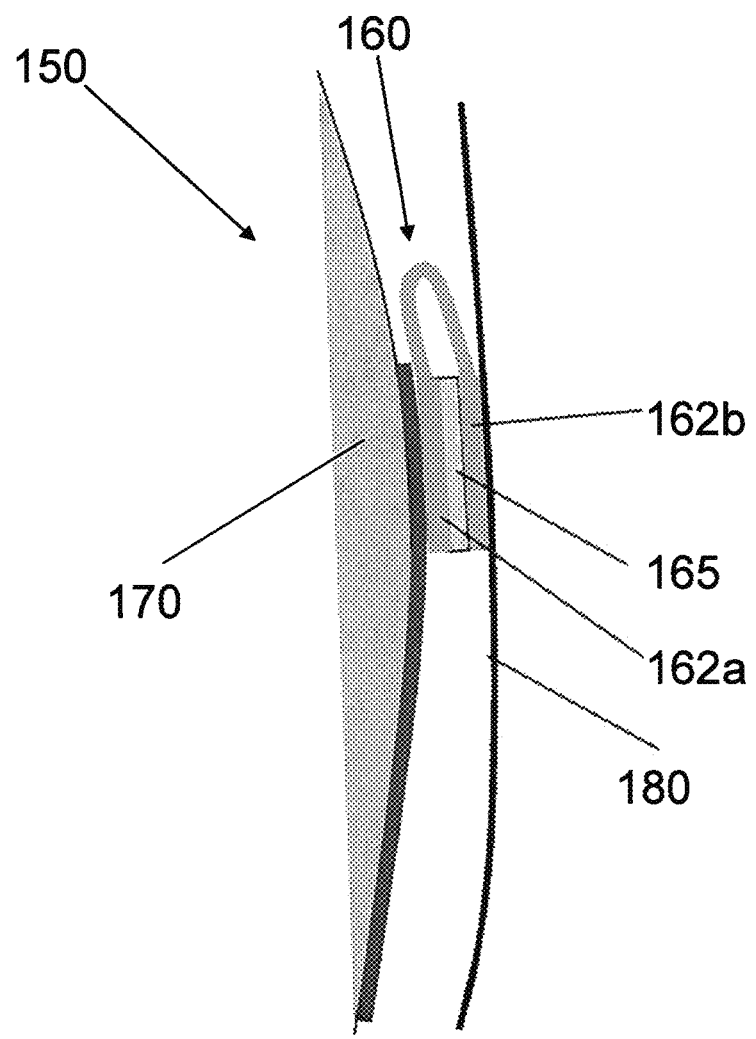
FIG. 1B illustrates an implementation of an example system including a force sensing element, according to the principles described herein.

FIG. 1B illustrates an example implementation of an example system 150 according to the principle herein. As illustrated in FIG. 1B, the example system 150 includes a force sensing element 160 is disposed on the flexible substrate 170 of an inflatable body is positioned proximate to a surface 180. In an example, the surface can be a portion of a tissue lumen, as described herein. The force sensing element 160 includes two conductive components 162a and 162b disposed substantially parallel to each other. An elastic dielectric component 165 is disposed between the two conductive components 162a and 162b. According to the principles herein, an amount of contact of the example system 150 with the surface 180 can cause an amount of force to be applied to the force sensing element 160. A measure of an electrical property of the conductive components provides an indication of the force applied to the flexible substrate 170. The measure of the force provides an indication of the degree of contact between the inflatable body and the surface 180.

Figure 2A:
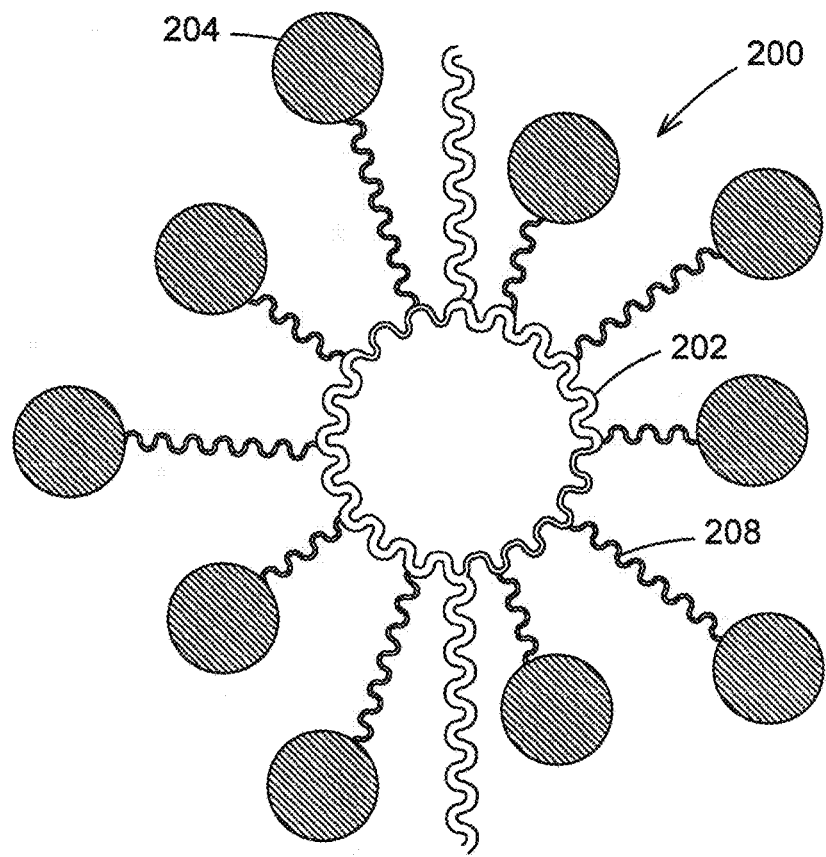
FIGS. 2A and 2B illustrate an example of a stretchable electronic system, according to the principles described herein.
Figure 2B:
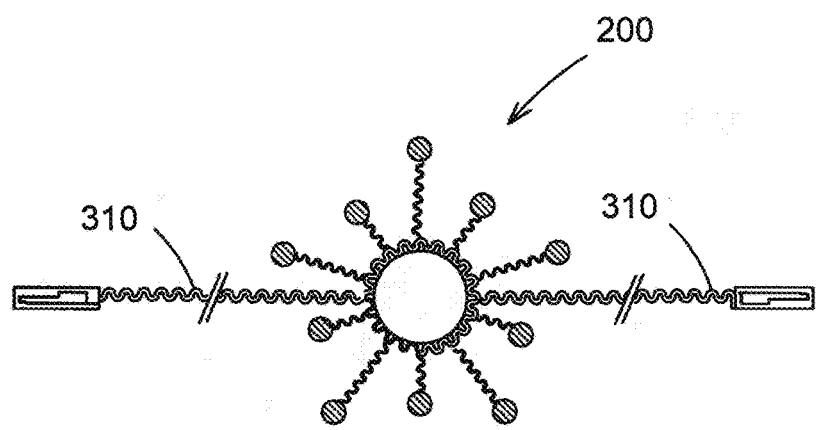

FIGS. 2A and 2B illustrate an example of a stretchable electronic system 200 that includes a coupling bus 202 and a number of force sensing elements 204. The stretchable electronic structure 200 can be coupled to an inflatable body according to the principles described herein. As shown in FIG. 2A, the force sensing elements can be configured to include capacitive-based force sensing elements 206. In the example configuration illustrated in FIG. 2A, there are 12 force sensing elements 204. However, other examples can include more or fewer force sensing elements 204. In the example of FIGS. 2A and 2B, the force sensing elements can be formed by at least two conductive plates, each of which is physically separated from the other by an elastic dielectric component. Each force sensing element 204 can be coupled to the coupling bus 202 via a coupling interconnect 208. The coupling interconnect is configured to be stretchable. For example, the coupling interconnect can have a serpentine configuration that facilitates the stretchability.

In the example of FIG. 2A, the force sensing element 204 are illustrated as having a substantially circular shape. In other examples, the force sensing element 204 can have rectangular, circular or other polygonal shape.

FIG. 2B shows a wider view of the example stretchable electronic system 200 of FIG. 2A, and shows the intermediate bus that can be used to couple the force sensing elements to a circuit to provide power to and/or collect measurements from, e.g., the force sensing elements 204. The intermediate bus and coupling interconnect in this any other example described herein can be formed from any suitable conductive material, including conductive materials described hereinabove.

As shown in FIG. 2A, the coupling bus 202 may have a non-uniform distribution about the loop structure. For example, portions of the coupling bus 202 that lead into the intermediate bus 210 are thicker than other portions of coupling bus 202.

Figure 3A:
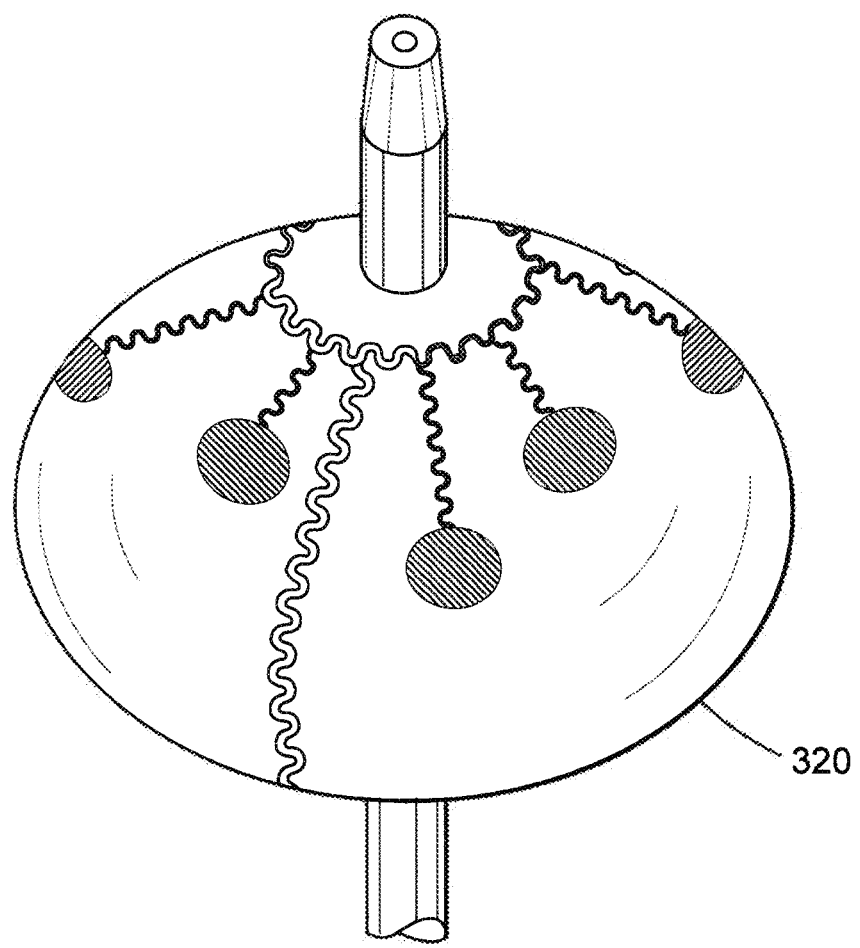
FIG. 3A shows the stretchable electronic system according to the principles of FIGS. 2A-2B, disposed on an example inflatable body, according to the principles described herein.
Figure 3B:
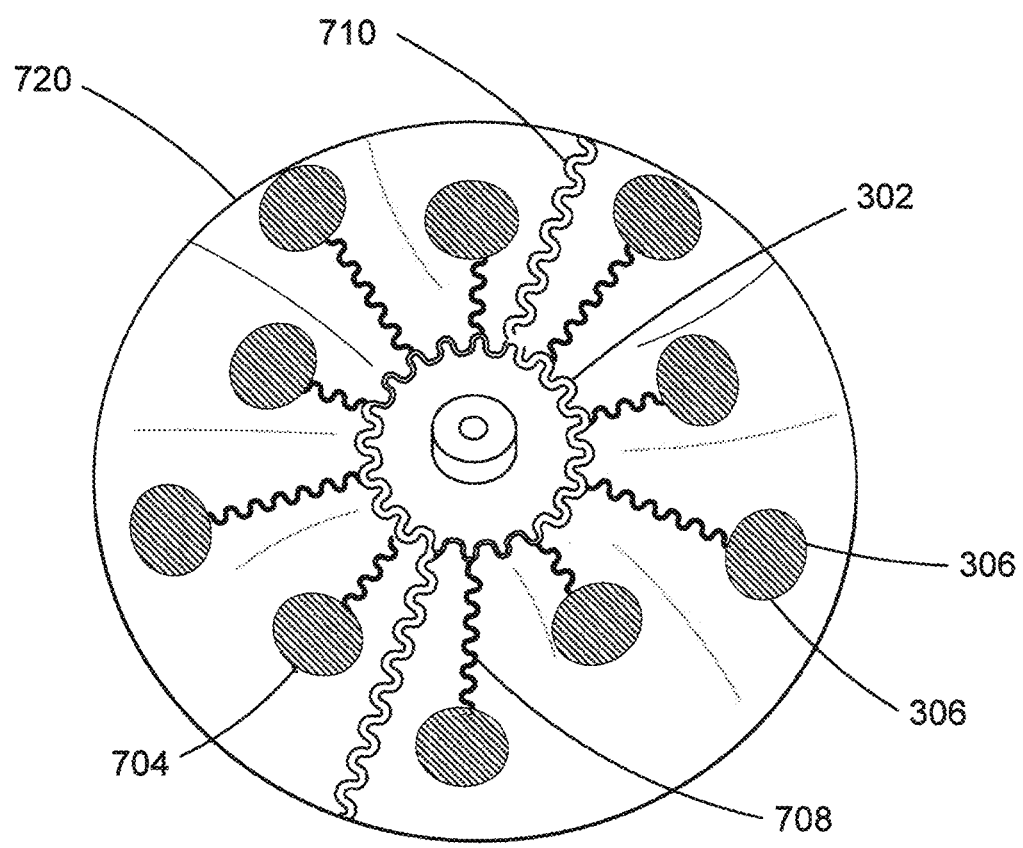
FIG. 3B is a different perspective view of the example balloon catheter of FIG. 3A, according to the principles described herein.

FIG. 3A shows the stretchable electronic system according to the principles of FIGS. 2A and 2B, disposed on an inflatable body 320. In this example, the inflatable body 320 is a balloon catheter. FIG. 3B is a magnified view of the balloon catheter of FIG. 3A. The stretchable electronic system includes a coupling bus 302, force sensing element 304, and coupling interconnects 308 and intermediate bus 310. The force sensing element 304 can be a capacitive-based force sensing element. To test the ability of contact sensors on a balloon to verify occlusion, an array 10 force sensing elements 304 can be implemented on an inflatable body to evaluate contact with the interior of a lumen. In some examples, the force sensing elements 304 can be strategically distributed about the inflatable body to be near points of potential contact. In an example system, the points for placement of the force sensing elements 304 can be determined as specific latitudes or circumferences of the inflatable body.

Figure 4B:
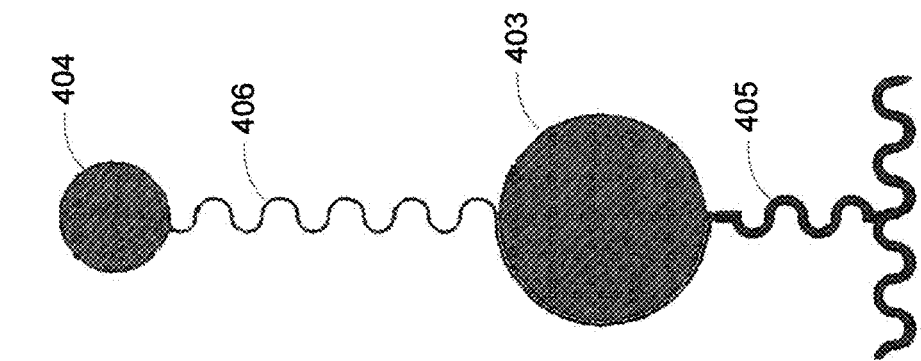
FIGS. 4A and 4B show example T-shaped force sensing element, according to the principles described herein.
Figure 4A:
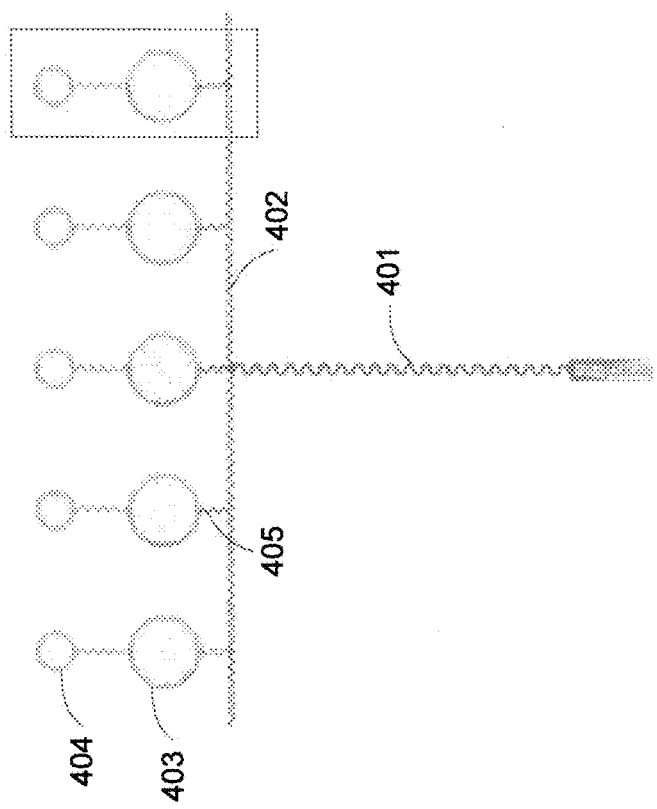

FIG. 4A shows an example configurations of a stretchable electronic system with a coupling bus 402 that has an open-loop structure that can be wrapped around at least a portion of an inflatable body.

As shown in FIG. 4A, the coupling bus 402 can have a serpentine configuration. In this non-limiting example, the coupling bus 402 is linear and the force sensing elements extend from the coupling bus 402. Each sensing element includes two conductive components 403 and 404, and an elastic dielectric component (not shown). The sensing elements extend from the coupling bus 402. In this example, the force sensing elements extend to a similar distance from the coupling bus, and in substantially the same direction. In other examples, the force sensing sensors can be fabricated to extend from the coupling bus to differing distances, and in differing directions. In this example, the sensing elements are coupled to the coupling bus 402 through coupling interconnects 405. To provide an apparatus with sensing elements that extend to differing distances from the coupling bus, the coupling interconnects 405 to each sensing element can be fabricated to have different lengths. In this example, a main bus 401 couples to the coupling bus 402 proximate to the midpoint of the coupling bus 402. Main bus can be used to provide electrical communication between the sensing elements and an external circuit, according to the principles described herein. In other example, the main bus may couple to the coupling bus 402 at any position that facilitates the electrical communication.

FIG. 4A illustrates a T-shaped force sensing elements configuration in accordance with various examples herein. The illustrated T-shaped configuration may be suited for an inflatable body with a longitudinal symmetry, including a cylindrical inflatable body or an oval inflatable body. In other examples, the system may be fabricated in a substantially closed form configuration, such as but not limited to a circular, ellipsoid, oval, or other polygonal arrangement. In these examples, the coupling bus can be fabricated in the closed form configuration, with the force sensing elements extending outwards or inwards from the coupling bus.

The stretchable electronic system of FIG. 4A illustrates a capacitive base force sensing element in unassembled form. As described in relation to FIG. 14A-14K below, the conductive components, the coupling bus, and the main bus can be fabricated a wafer using fabrication techniques in the art. As illustrated in FIG. 4A, the conductive components 403 and 404 are coupled by a coupling component 406. Coupling component can be a non-conductive material that serves to maintain the relative position of conductive components 403 and 404. The elastic dielectric component can be applied to the conductive component 403 and/or conductive component 404 prior to assembly. The conductive components are then disposed substantially parallel to one another, with the dielectric component disposed between then, to provide a force sensing element.

In one example, the example apparatus of FIG. 4A can be disposed on the flexible surface of an inflatable body prior to assembly of the conductive components and the dielectric component to provide the force sensing element. For example, the coupling bus 402 and conductive component 403 can be disposed on the flexible surface of an inflatable body in a first stage. In a second stage, a conductive component 404 can be positioned substantially parallel to its respective conductive component 403, with a dielectric component disposed between them, to provide the assembled force sensing element. In another example, each conductive components 404 can be positioned substantially parallel to its respective conductive component 403, with a dielectric component disposed between them, to provide the assembled force sensing elements prior to being disposed on the flexible surface of an inflatable body.

FIG. 4B illustrates and enlarged view of an unassembled force sensing element. As illustrated, the conductive component 403 is coupled to the coupling bus 402 by the coupling interconnects 405. Conductive component 404 is coupled to conductive component 403 using a coupling component 406. In an example, the coupling interconnects 405 can include a conductive stretchable interconnect and a non-conductive layer, where the conductive stretchable interconnect facilitates electrical communication between the force sensing element sand the coupling bus.

The main bus 401, coupling bus 402, coupling interconnects 405, and coupling component 406 are illustrate in FIGS. 4A and 4B as having a serpentine configuration. Such as configuration provides both flexibility and stretchability to the system. As a result, the example systems and apparatus described herein can conform and adjust to any conformation of the inflatable body, from a deflated or retracted state to a fully inflated or expanded state, without affecting the functioning of the force sensing elements according to the principles described herein. In other examples of a system or apparatus herein, any one or more of the main bus 401, the coupling bus 402, the coupling interconnects 405, or the coupling component 406, can be fabricated in a zig-zag configuration or a rippled configuration or other configuration that provides stretchability.

In another example, the coupling component 406 can include the conductive stretchable interconnect to facilitates electrical communication between the force sensing element sand the coupling bus. In this example, the conductive portion of coupling component 406 can be insulated from conductive component 403. For example A portion of the stretchable interconnect 406 can be cause to run along the circumference of the conductive component 403, with the interconnect 406 remaining electrically isolated from the conductive component 403.

Figure 4C:
FIGS. 4C and 4D show example assembled force sensing element with both conductive components 408 separated by a dielectric material, according to the principles described herein.
Figure 4D:
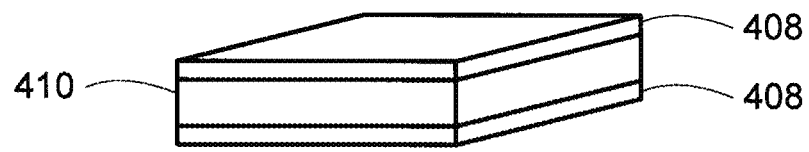

In the examples of FIGS. 4A and 4B, the first conductive component 403 is illustrated larger in area than the second conductive component 404. In another example, the conductive component can be fabricated to be of the same size. For example, FIG. 4C shows an example of an assembled force sensing element with both conductive components 408 separated by a dielectric material 410 and having substantially the same area. According to the principles described herein, the conductive components can have other shapes. For example, FIG. 4D show an example where the assembled force sensing element is formed from conductive components with a rectangular shape.

In some example implementations, the surface area of the conductive components can be fabricated to have an area between about 1 mm$^2$ and about 4 mm$^2$.

Figure 5C:
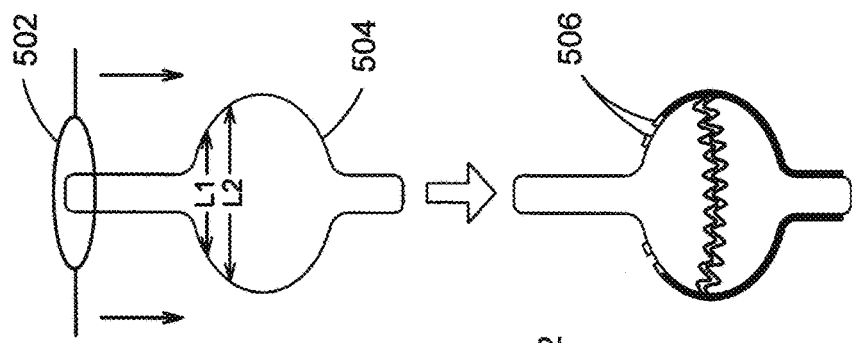
FIGS. 5A-5C illustrate the assembly of an example stretchable electronic system, according to the principles described herein.
Figure 5B:
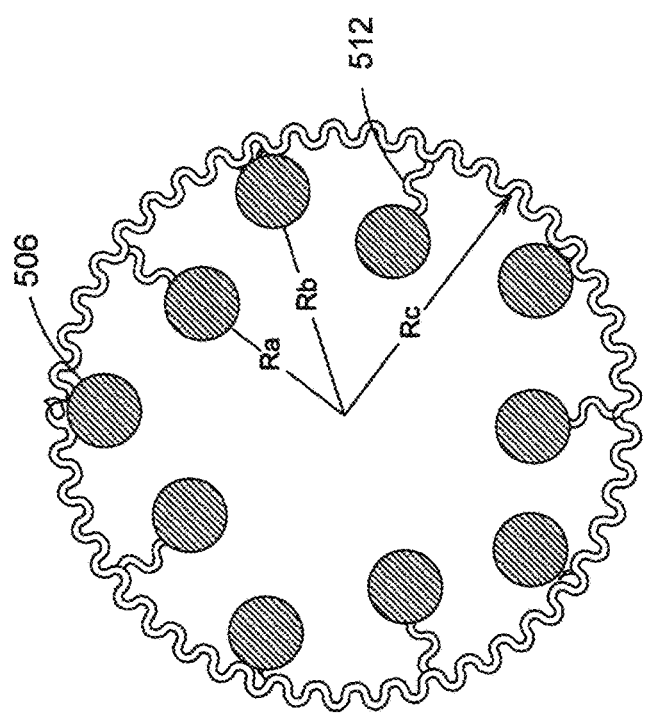
Figure 5A:
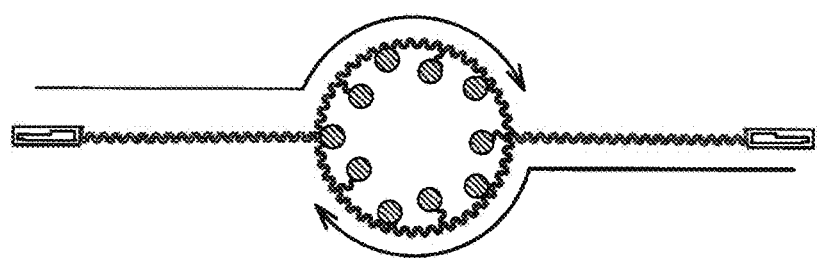

FIG. 5A shows an example of the force sensing elements where the coupling bus is formed as a closed form, with the sensing elements extending towards the center of the closed form. As shown in the example of FIG. 5B, the system can be fabricated such that the force sensing elements extend to two different distances. In a non-limiting example, the inflatable body can be an ARCTIC FRONT® Cryoballoon Catheter (available from Medtronic Inc, Minneapolis, Minn.) balloon. In this example, the force sensing elements can be positioned at about the 15 mm and about the 20 mm diameter portions of the cryoballoon (as described in greater detail in FIGS. 5A-5C). In the non-limiting example of FIG. 5B, the radius ($R_C$) of the coupling bus 506 is around 12 mm, a first set of the force sensing elements can be fabricated to extend from the coupling bus 506 to fall along a circle of a radius ($R_B$) of about 10 mm, and a second set of the force sensing elements can be fabricated to extend from the coupling bus 506 to fall along a circle of a radius ($R_A$) of about 7.5 mm. The density of sensing elements facilitate identification of spatial gaps in occlusion between the inflatable body and target lumen.

An interconnect having a serpentine structure as described herein allows for stretching and compression of the system, ensuring survival of the force sensing elements during deployment through a sheath. In an example implementation, the force sensing elements can be each about 1 mm$^2$ in total area, to achieve sufficient contact with tissue. These configurations of the stretchable electronic system also employ coupling buses or annular interconnects at or near the distal end of the inflatable body. In the configurations provided in FIGS. 2A-3B, the coupling bus or annular interconnect is positioned at smaller radius than the force sensing elements. In the example of FIG. 5A-5C, the coupling base or annular interconnect is positioned at a larger diameter than the force sensing elements.

FIGS. 5A-5C illustrate the assembly of an example stretchable electronic system 502 (shown in FIGS. 5A and 5B) with an inflatable body 504. In the example of FIG. 5C, of the stretchable electronic system 502 is configured such that the coupling bus is disposed near an equator of inflatable body 504, and the force sensing elements 506 are directed towards closer to distal portions of the inflatable body 504. The differing radii of extent of the force sensing element are configured such that they fall at specified latitudes of the inflatable body 504. For example, the stretchable electronic system can be configured (based on the differing lengths or differing capacities for stretchability of the flexible interconnect structures 512) such that a given sensing element 506 is disposed at latitude L1 or latitude L2 of the inflatable body 504. FIG. 5C illustrates an assembly process for integrating a stretchable electronic system that includes a substantially circular coupling bus or annular interconnect with an inflatable body 504. As noted herein, the substantially circular coupling bus or annular interconnect facilitates alignment during integration of the flexible electronic components with the inflatable body 504.

In an example, using a balloon catheter, the latitude L1 can be positioned at a level of the balloon catheter with a circumference that is about 65% of the circumference of the equator of the balloon, while the latitude L2 can be positioned at with a circumference that is about 87% of the circumference of the equator. The latitude(s) of placement of the force sensing elements of a stretchable electronic system on an inflatable body can be determined based on an expected contact point between the inflatable body and a region of a tissue lumen. For example, as shown in FIG. 1A, portions of an inflatable body 104 may be expected to substantially contact portions of a tissue lumen 102. The position of placement of the force sensing elements can be determined such that one or more of the force sensing elements are positioned proximate to the tissue when the inflatable body is deployed in the tissue lumen. The latitudes (e.g., L1, L2, etc) may be decided based on such expected positioning of the inflatable body relative to the tissue lumen.

Figure 6B:
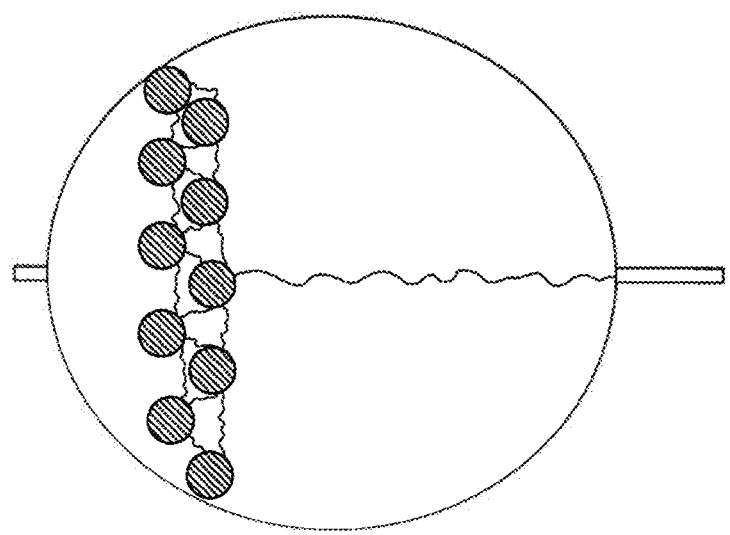
FIGS. 6A-6B are example diagrams illustrating the balloon inflation/deflation process, according to the principles described herein.
Figure 6A:
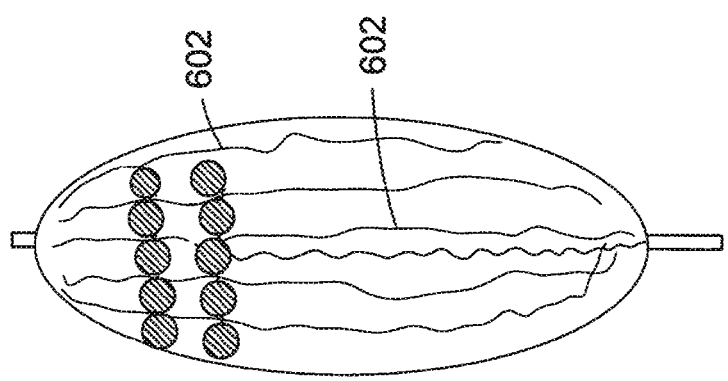

FIGS. 6A and 6B illustrate examples of a stretchable electronic system disposed about an inflatable body such that the force sensing elements 1704 are positioned at two different latitudes. FIGS. 6A and 6B also illustrate the inflation/deflation process of the inflatable body. As shown, the inflatable body can be configured such that small ridges 602 can form on the inflatable body surface in a deflated state, facilitating for better folding of the inflatable body. According to the principles herein, and as illustrated in FIG. 6A, the plurality of sensing elements can be disposed about the inflatable body such that the force sensing elements are disposed at areas of minimal curvature of the inflatable body in a deflated state (which includes a collapsed state). The conformal force sensing elements are strategically and selectively disposed between the ridges 602 at areas of minimal curvature in the deflated state, to minimize applied strain on the force sensing elements. Upon inflation of the inflatable body, the force sensing elements are deployed in a staggered fashion on the flexible surface of the inflatable body.

Figure 7C:
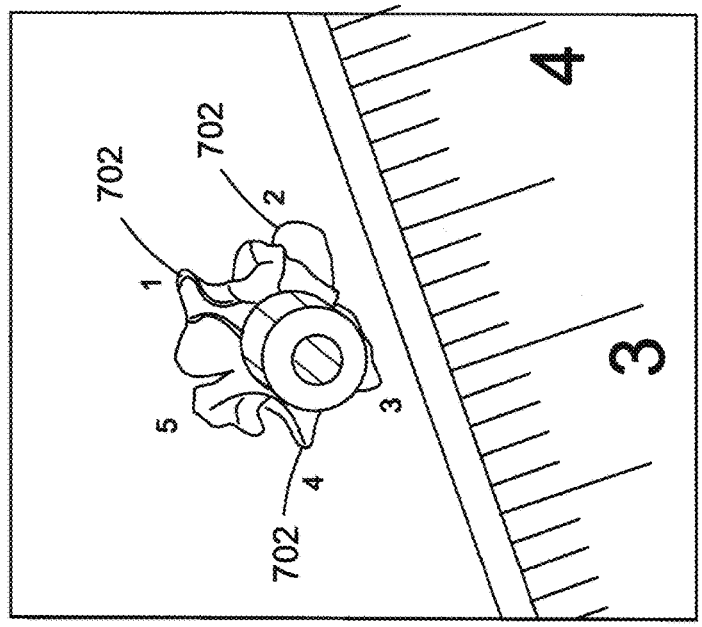
FIGS. 7A-7C illustrates another example of a catheter balloon transitioning between an inflated and deflated state, according to the principles described herein.
Figure 7B:
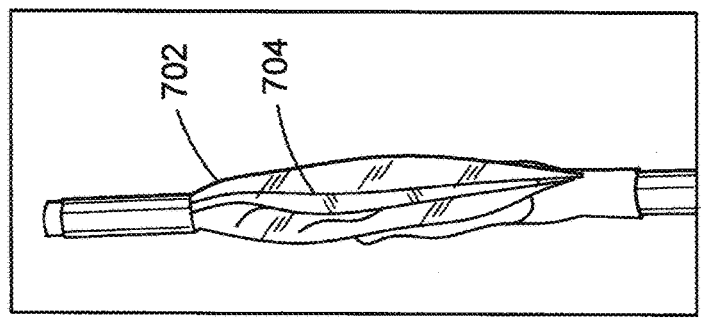
Figure 7A:
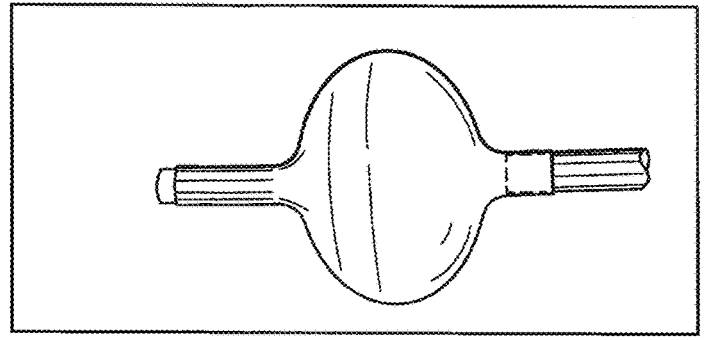

FIGS. 7A-7C illustrate an example where the inflatable body is a balloon catheter. FIGS. 7A and 7B shows the transitioning of the balloon catheter between an inflated state (FIG. 7A) and a deflated state (FIG. 7B). The example balloon catheter of FIGS. 7A-7C has an "onion" shape in the inflated state (a pear-shaped with a curvilinear morphology). Such a balloon may be configured to deflate and to form approximately an average of about five (5) clover-shaped folds. That is, the ridges 702 in the deflated state extend into the points of the clover-shaped folds, and portions of the balloon between the ridges, the recesses 704, are disposed closer to the catheter shaft when the balloon is in the deflated state.

The determination of the configuration of the force sensing elements on the surface of an inflatable body includes analysis of high and low strain regions of the inflatable body in the deflated state to determine locations on the inflatable body to situate sensing elements so that they experience minimal stress and/or strain, as demonstrated further in connection with FIGS. 6A-B and 7A-7C. Finite element analysis of the stress-strain profiles also enables mechanical optimization such that the force sensing elements are located in the area of minimal curvature of the inflatable body, thereby minimizing failure modes during operation (for example, when the inflatable body is being introduced into a tissue lumen prior to being deployed near a tissue region of interest).

Figure 8:
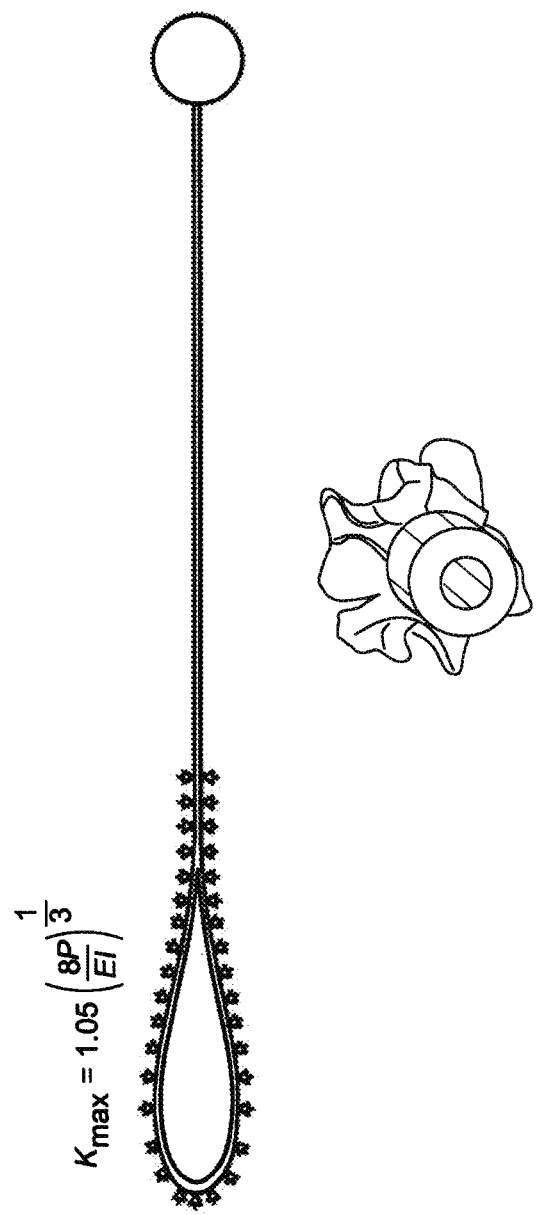
FIG. 8 is a schematic of a folded section of an example deflated balloon, according to the principles described herein.

FIG. 8 is a schematic of a folded section of an example balloon catheter in a deflated state. When a balloon catheter is not pressurized (e.g., in the deflated state), the balloon may form a plurality of folds. FIG. 8 depicts one example of such folds with respect to the catheter shaft. FIG. 8 also shows a mathematical function that can be used to model the curvature (Kmax) at any point on the fold of the example balloon catheter is represented by the equation Kmax=1.05 $(8/E \times I)^{1/3}$, where p is approximately atmospheric pressure, E is the Young's modulus of the material of the balloon, and I is the moment of inertia of the balloon catheter.

FIG. 9 shows a graph illustrating the different in computed strain along a folded section of a deflated balloon. In the example of FIG. 9, the arc length from the left point of the balloon to the k=0 location is computed at about s=0.75 mm. The curvature at the left end of the balloon is computed at about 4940 $m^{-1}$ (the maximum of all computed curvature values). The curvature of the balloon at the right end is computed at about 823 $m^{-1}$. As shown in FIG. 9, higher strain regions and lower strain regions (including regions of substantially zero strain) of the inflatable body can be determined. Based on the modeling of the curvature of the balloon in the deflated state, the region on the fold of minimal curvature for the balloon can be determined.

According to the principles herein, based on a model of the expected or predicted folding behavior of an example inflatable body on deflation or collapse, an example stretchable electronic system may be configured, fabricated and integrated with an inflatable body such that the force sensing elements are disposed proximate to regions of minimal curvature of the inflatable body (when in a deflated state). For any example inflatable body according to the principles described herein, the folding (or collapsing) behavior of the inflatable body can be modeled or determined based on a number of training samples of the inflatable body, where a pattern of average or most likely folding behavior is determined. As illustrated in FIG. 9, higher strain regions and lower strain regions (including regions of substantially zero strain), including regions of minimal curvature, of the inflatable body can be determined. The flexible interconnect that lead from the force sensing elements to the coupling bus can be disposed on the inflatable body so that they traverses the regions of maximal curvature.

Figure 10:
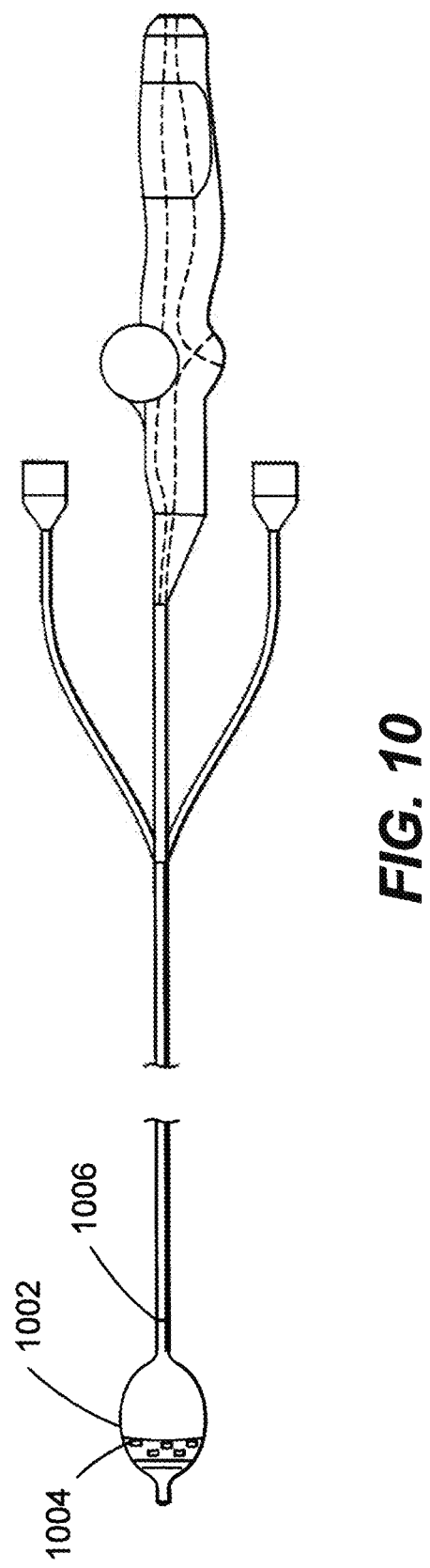
FIG. 10 is a schematic illustrating an example balloon catheter integrated with a flexible sensing element configuration, according to the principles described herein.

FIG. 10 shows an example schematic diagram of a balloon catheter integrated with a stretchable electronic system 1004 according to the principles herein. In the illustrated example, the force sensing elements are positioned on the distal portion of the balloon 1002. The stretchable electronic system 1002 is coated with a polyurethane encapsulant layer. The polyurethane coated balloon is implemented with a catheter that includes a flexible printed circuit board (PCB) interconnection 1006. In an example, the PCB interconnections may be bonded to the catheter. The electrical leads from the PCB interconnections may extend to a connecter housing, which housing may be disposed exterior to the catheter.

Figure 11:
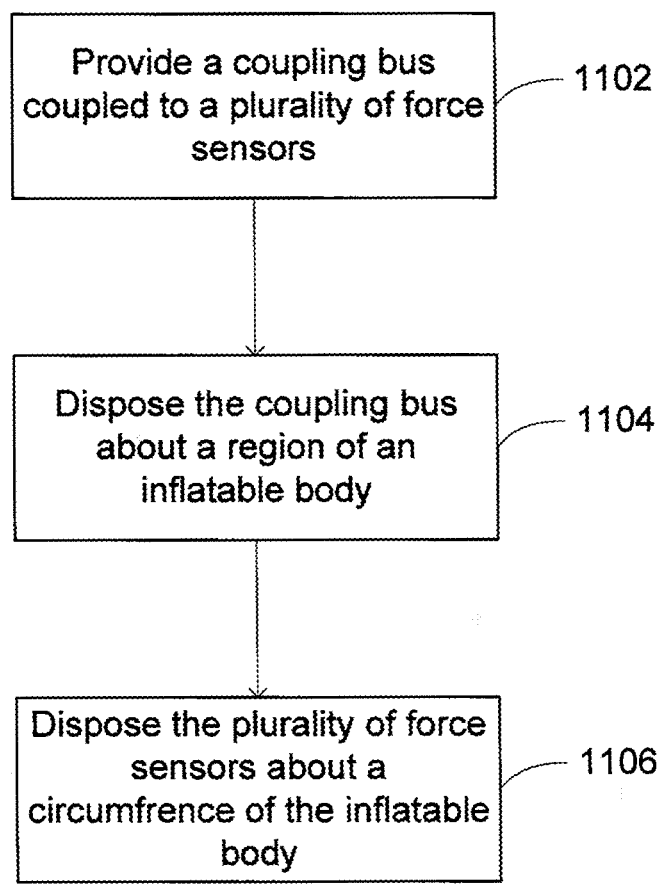
FIG. 11 is a flow chart illustrating a non-limiting example process for fabricating an stretchable electronic system and integrating the stretchable electronic system with a balloon catheter, according to the principles described herein.

FIG. 11 shows a flow chart illustrating a non-limiting example process for fabricating a stretchable electronic system and integrating the stretchable electronic system with an inflatable body. In block 1102, a coupling bus that is couple to a plurality of force sensing elements is provided. In this example, the force sensing elements include at least two conductive components disposed substantially parallel to each other and separated by an elastic dielectric. In block 1104, the coupling bus is disposed about the inflatable body. In block 1106, the force sensing elements are disposed onto the inflatable body. In this example, the force sensing elements are placed about a portion of a circumference of the inflatable body.

Figure 12:
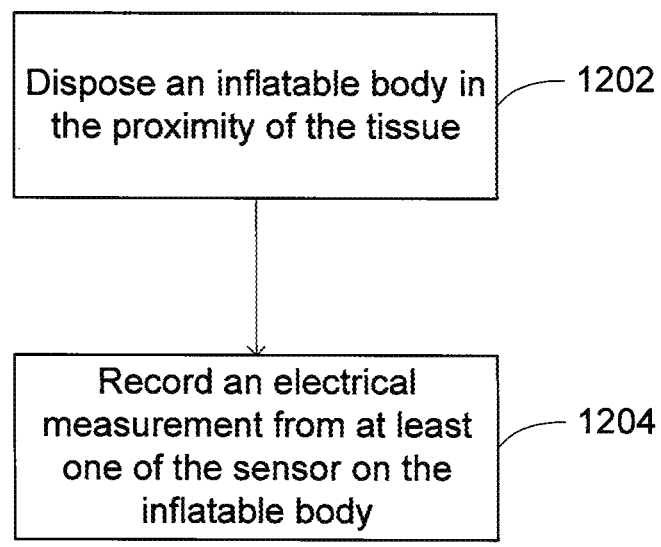
FIG. 12 is a flow chart illustrating a non-limiting example process of performing a medical diagnosis and/or treatment on a tissue, according to the principle described herein.

FIG. 12 shows a flow chart illustrating a non-limiting example process for performing a medical diagnosis or treatment on a tissue. In block 1202, an inflatable body is disposed in the proximity of the tissue to be treated or diagnosed. In this example, the inflatable body includes a coupling bus and a plurality of force sensing elements. Each of the force sensing elements can be connected to the coupling bus. In block 1204, an electrical measurement recording of at least one of the sensors is made. In this example, the measurement provides an indication of the force applied to the inflatable body.

Figure 13:
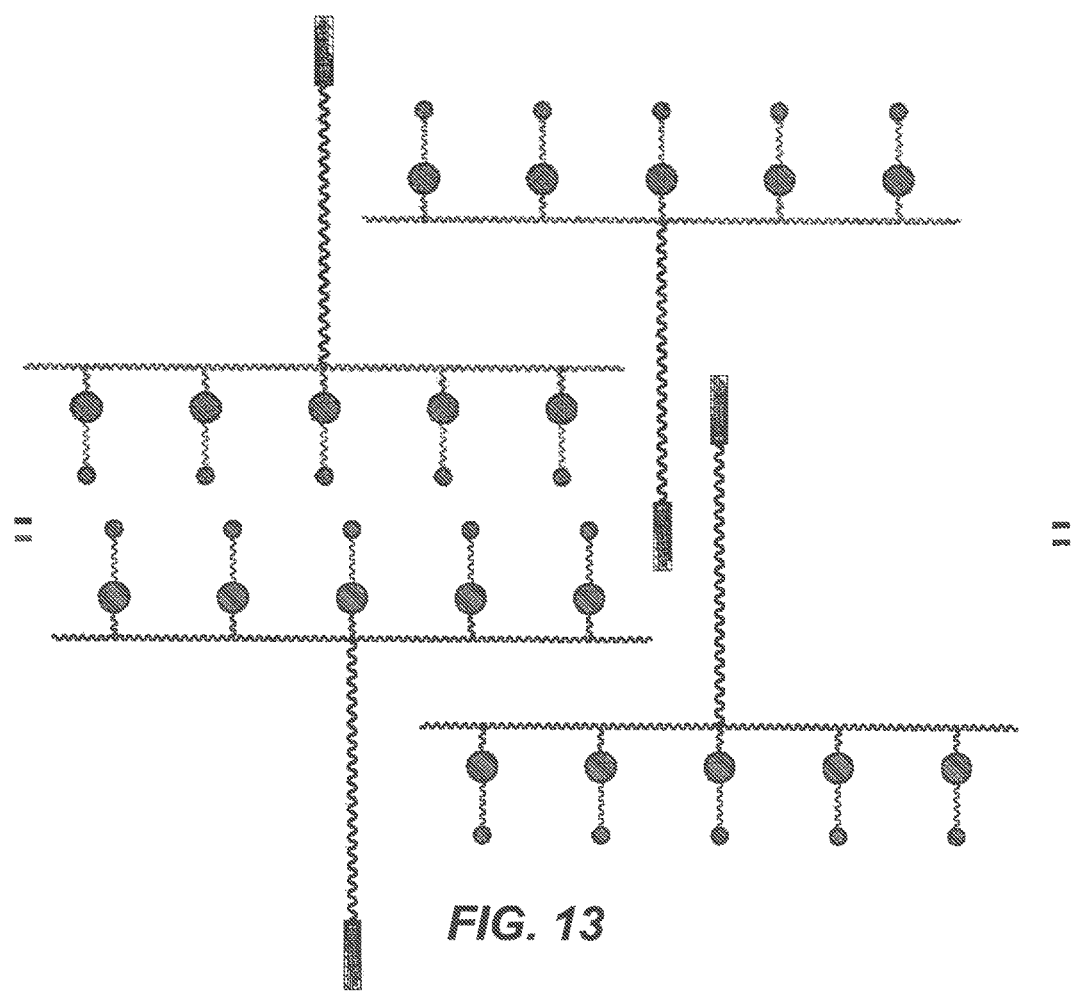
FIG. 13 illustrates a non-limiting example arrangement of T-shaped force sensing element on a fabrication wafer, according to the principles described herein.

FIG. 13 shows a non-limiting example arrangement of T-shaped force sensing element on a fabrication wafer. The arrangement allows for a greater yield of force sensing elements from a single fabrication wafer.

To facilitate conformality of a sensing apparatus according to various examples disclosed herein, the flexible substrate of a conformal sensing apparatus may be formed of a plastic material or an elastomeric material, including any of a wide variety of polymeric materials. The bottom terminus of the "main bus" of the T-configuration is coupled to a flexible printed circuit board ("flex PCB") disposed along the shaft of the catheter. As noted below, the interface between the bottom terminus of the main bus and the flex PCB includes various examples. Small wires to carry signals "off-catheter" can be attached to the flex PCB via solder connection.

In one implementation, each force sensing element is wired individually (i.e., two conductors/sensor) such that a pair of wires are available "off-catheter" for each sensor. Working from "off-catheter" to the contact sensors themselves, and considering an example involving five contact sensors, ten wires are soldered to the flex PCB, and the traces on the flex PCB are designed such that there is approximately a "one-finger distance" between respective solder points (to facilitate assembly by hand).

The interface between the main bus of the T-configuration and the flex PCB involves the mechanical and electrical coupling of 10 contact pairs via a specially selected adhesive and contact layout. In this non-limiting example, the main bus includes 10 conductors electrically insulated from each other, and two of these conductors that are electrically coupled to a central sensor situated at the intersection of the main bus and the horizontal top bar of the T-configuration.

Four conductors then travel down the serpentine bus to the left of the central sensor (for the two additional sensors to the left of the central sensor), and four conductors travel down the serpentine bus to the right of the central sensor (for the two additional sensors to the right of the central sensor). The "outermost" portions of the serpentine bus on the far left and far right arms each carry two conductors for the outermost left and right sensors.

A non-limiting example of fabrication of an example system or apparatus is described. FIGS. 14A-14K illustrate cross sectional views of an example process for fabrication of an apparatus including force sensing element according to the principles herein, such as but not limited to the apparatus illustrated in any of FIGS. 1A-6B and 13. FIGS. 14A-14K illustrate and example of the fabrication of the conductive components, the disposing of the dielectric component on the conductive components, and the positioning of the conductive components relative to each other to form the force sensing elements.

Figure 14:
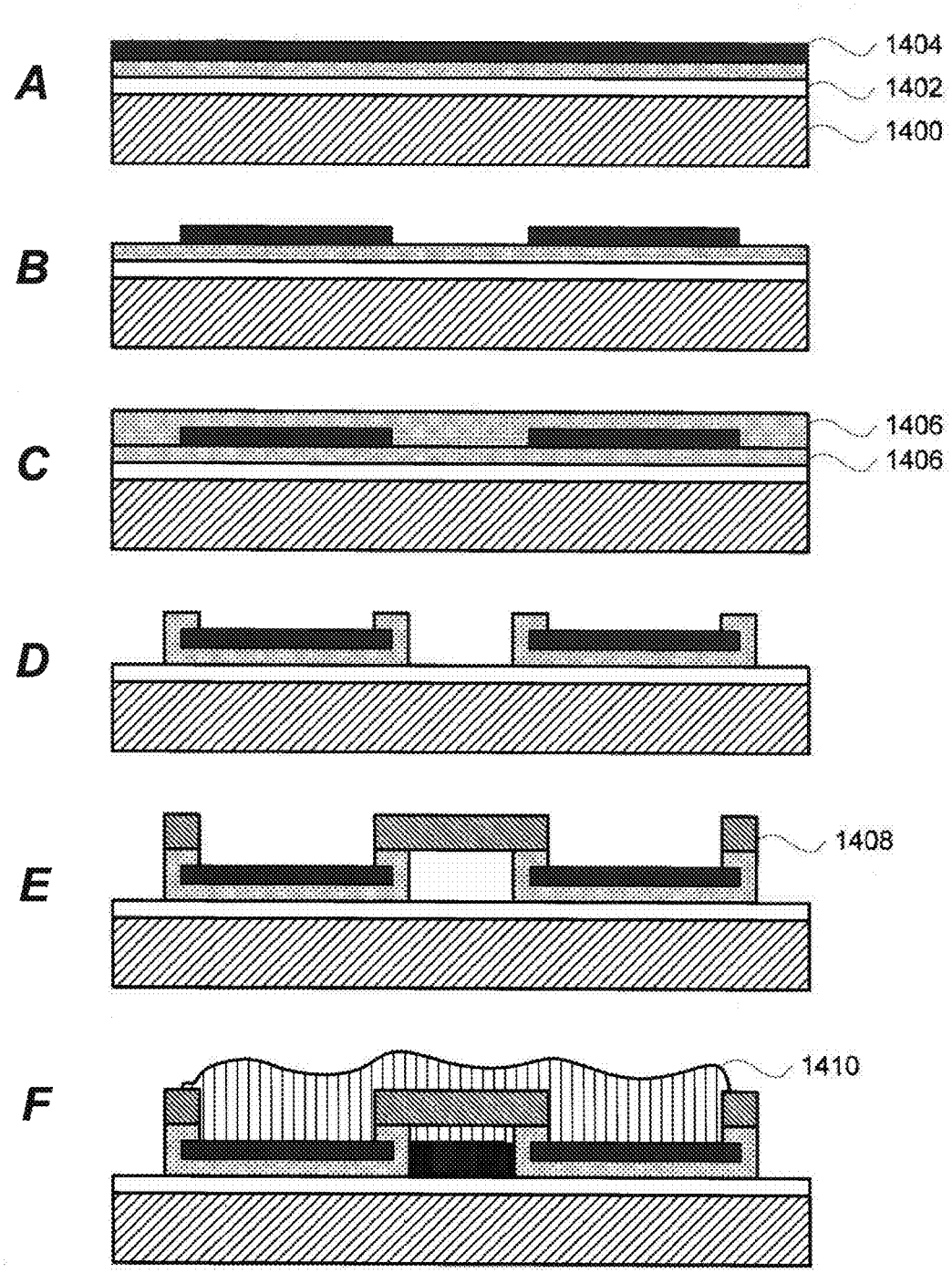
FIGS. 14A-14K illustrates a series of cross section of an example process for fabricating a capacitive-based force sensing element, according to the principles described herein.
Figure 14:
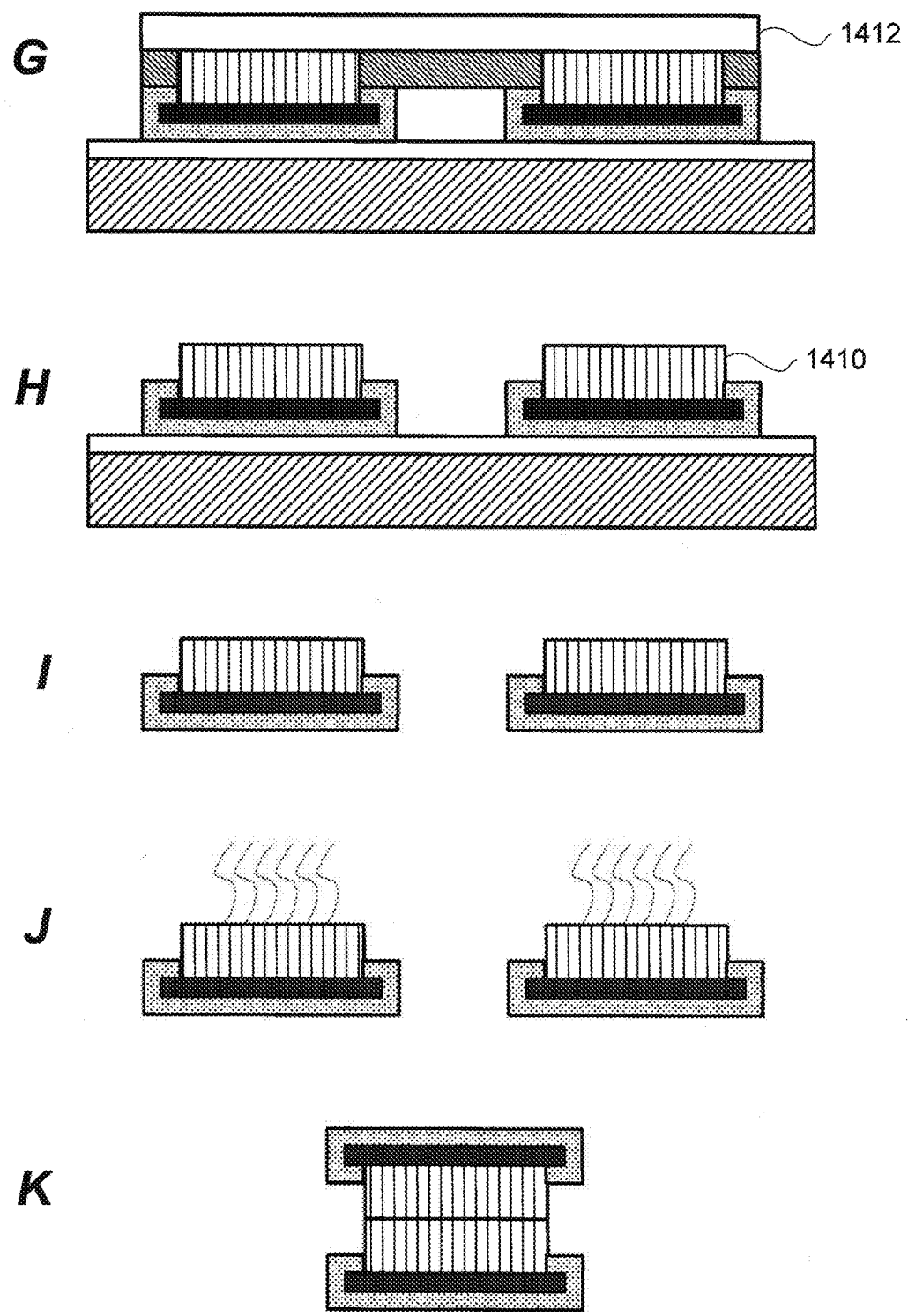

Block 1. FIG. 14A shows a substrate 1400. In this example, the initial substrate can be a fabrication wafer, such as but not limited to a silicon wafer. As illustrated in FIG. 14A, an intermediate layer 1402 can be disposed on the substrate 1400 prior to deposition or evaporation of a layer of conductive material 1404. For example, the intermediate layer can be a sacrificial layer of a polymer material, such as bit not limited to a polyimide or polymethylmethacrylate (PMMA). The intermediate layer can be applied by spin coating.

Block 2. As illustrated in FIG. 14B, the layer of conductive material 1404 can be patterned to generate the conductive components of the force sensing element.

Block 3. As illustrated in FIG. 14C, a second layer 1406 can be deposited over the conductive material and the intermediate layer 1406. In this example, the second layer 1406 encapsulates the conductive components. The second layer 1406 can be a polymer layer Block 4. As illustrated in FIG. 14D, the intermediate layer 1402 and second layer 1406 can be patterned using reactive ion etching. The etching of the second layer 1406 creates a channel 1407 to the conductive components.

Block 5. As illustrated in FIG. 14E, a mask 1408 can be applied. In this example, the mask is disposed on the second layer 1406, leaving the conductive components exposed. In this example, the mask provides thickness control for the elastic dielectric that is applied.

Block 6. As illustrated in FIG. 14F, an elastic dielectric material 1410 is cast onto the mask 1408 and within the channel 1407 generated by the etching. In a non-limiting example, the dielectric, material can be a silicone.

Block 7. As illustrated in FIG. 14G, an additional layer 1412 can be applied over the mask 1408 and dielectric material 1410 to assist with the filling of the channel 1407. For example, a glass wafer can applied and pressure is applied to the glass wafer. In this example, the pressure on the glass wafer ensures the elastic dielectric material completely fills the channel 1407.

Block 8. As illustrated in FIG. 14H, the additional layer 1412 and the mask 1408 are removed. In this example, the mask 1408 can be used to ensure the elastic dielectric component is applied to the conductive components of the force sensing element.

Block 9. As illustrated in FIG. 14I, the fabricated apparatus is separated from the fabrication wafer. In this example, the intermediate layer 1406 is removed to liberate the fabricated apparatus. As a non-limiting example, where the intermediate layer 1406 includes PMMA, the PMMA can be removed using acetone. FIG. 14I also shows that portions of the conductive components can be coated with a layer 1411 of, e.g., a polyimide, in the fabrication process.

Block 10. As illustrated in FIG. 14J the exposed elastic dielectric material can be surface treated to improve its adhesive capability. For example, the dielectric material can be treated with an $O_2$ plasma. In this example, the $O_2$ plasma treatment can be used to clean the exposed surfaces and aids in the bonding of the elastic dielectric disposed on the first conductive component to the elastic dielectric disposed on the second conductive component. In another example, the elastic dielectric material can be applied to only one of the conductive component plates.

Block 11. As illustrated in FIG. 14K the one of the conductive component can be disposed substantially parallel to the other conductive component, with the dielectric component disposed in between to provide a force sensing element. In some example implementations, one conductive component can be disposed over the other conductive component manually, such as but not limited to, with the use of a microscope. In another example, a dissolvable tape can be applied to the underside of one of the conductive components (e.g., to the conductive component farthest from the coupling bus) and used to position it relative to the other respective conductive component. In an example where the apparatus is fabricated in a "T" configuration, each of the conductive components disposed farther away from the coupling bus can be adhered to the dissolvable tape, and folded onto its respective second conductive component in unison. In another example, a water soluble tape can be applied to the horizontal bar of the "T" once the conductive plates have been coupled together with the dielectric material, to facilitate the placement of the stretchable electronic system on the inflatable body.

Figure 15:
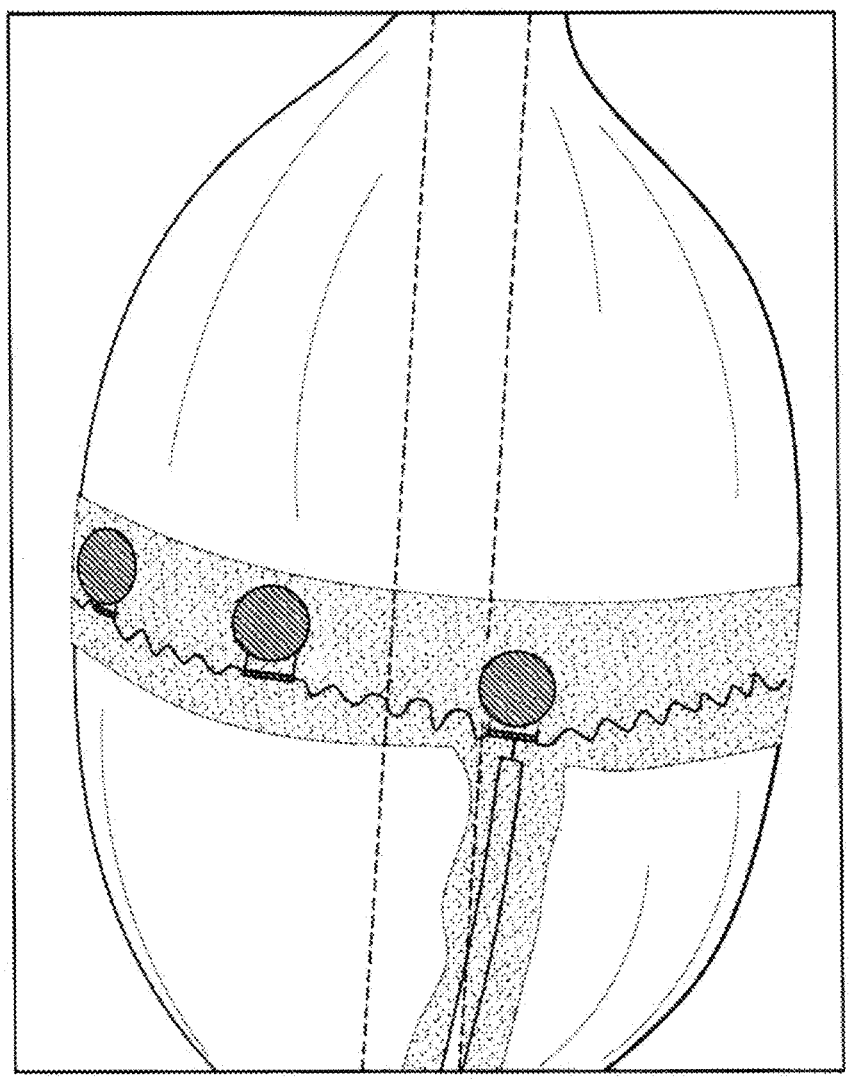
FIG. 15 illustrates an example T-shaped force sensing element disposed over an inflatable body, according to the principles described herein.

FIG. 15 shows an example of a stretchable electronic system having a "T-configuration," such as the electronic system of FIG. 4A, coupled to an inflatable body, such as a catheter balloon.

The main bus can be made narrow (e.g., <1-2 mm) in order to achieve a smooth transition from the catheter shaft to the surface of the balloon. The more conductors, the more lateral width is added to the main bus. Fewer serpentine interconnects may be disposed along the main bus given the vertical orientation.

Because most of the strain occurs along the horizontal direction during inflation, and not the vertical in most ellipsoidal and spheroidal balloons, an example configuration includes keeping the length of the main bus minimized (impedance low) and the width as narrow as possible.

The main bus can be made wavy to allow for stretching during balloon inflation/deflation. Alternatively, a straight main bus can be flexible but not stretchable. The wavy design can be used to place sensing elements distal on the balloon, as the main bus may travel over a greater balloon curvature.

The sensors and serpentines can be microfabricated during the same process of polymer and metal vapor deposition. They can be deposited in sequential layers. The discrete sensors may be picked and placed onto the underlying metal interconnect layers, thus forming a network of metal interconnections with discrete sensor units.

Serpentine interconnects can have greater curvatures to allow for more stretching. The coupling busses and interconnects described herein cab be formed of interconnects with a serpentine geometry. Optimal designs can be based on the balloon geometry, sensing element placement, and folding behavior for inflation/deflation.

The degree of force can be determined by measuring at least one of the conductive components of the force sensing element. The two conductive components are separated by an elastic dielectric, such that when a force is applied to at least one of the conductive components, the distance between the conductive components may reduce. An electrical measurement of the at least one of the conductive components can provide an indication of the force applied to the force sensing element.

In some examples, temperature sensors also can be disposed on the flexible surface of the inflatable body. The temperature sensors can provide real-time temperature data during cryoablation or RF ablation.

Monitoring tissue temperature can provide estimate of lesion depth/quality. LEDs can be disposed on the balloon to provide illumination.

Balloon shapes from different manufactures may differ, and size, geometry, placement/orientation of sensor assembly can be customized on different balloons. In one example, sensors can be placed distal on balloon for pulmonary vein isolation (PVI) monitoring. Different stretch behavior may exist for balloon inflation/deflation. In one example, very small ridges exist on a Cryoballoon manufactured by a particular manufacturer, which may experience more stretching between inflation and deflation. The surface area of a deflated balloon may limit the size and number of sensing elements. In one example, the sensing elements are staggered diagonally to fit more on a deflated balloon. The sensing elements can spread out into a line upon inflation.

In one example, the sensing elements are staggered in two rows, or as vertical lines on the balloon, as described in the related patent applications. In another example, signal filters and gain adjustment can be used to amplify signal amplitudes.

Figure 16A:
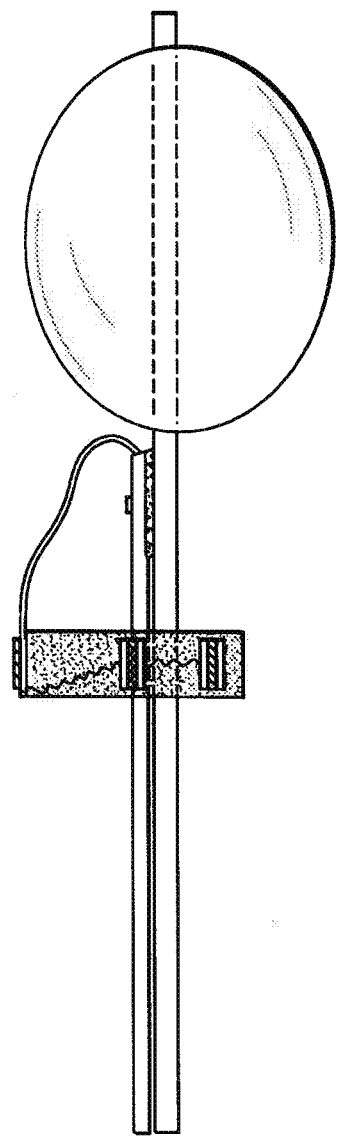
FIGS. 16A-16C illustrate a series of stages of an example fabrication process of attaching a T-shaped force sensing element to a balloon catheter, according to the principles described herein.
Figure 16B:
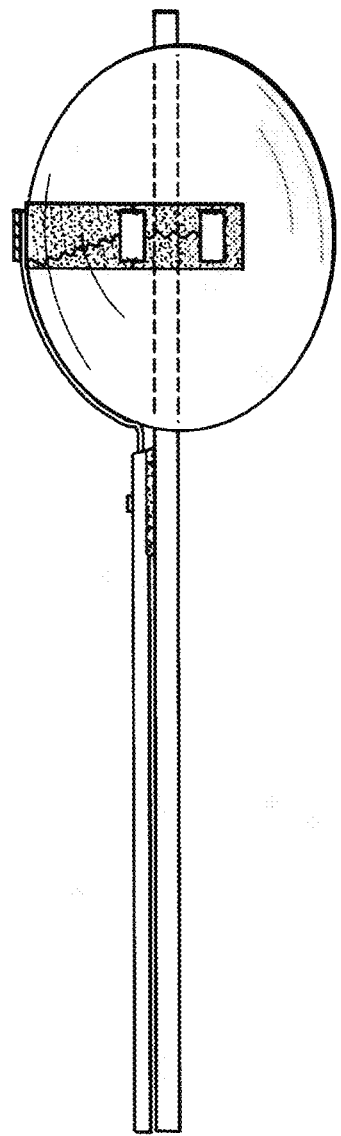
Figure 16C:
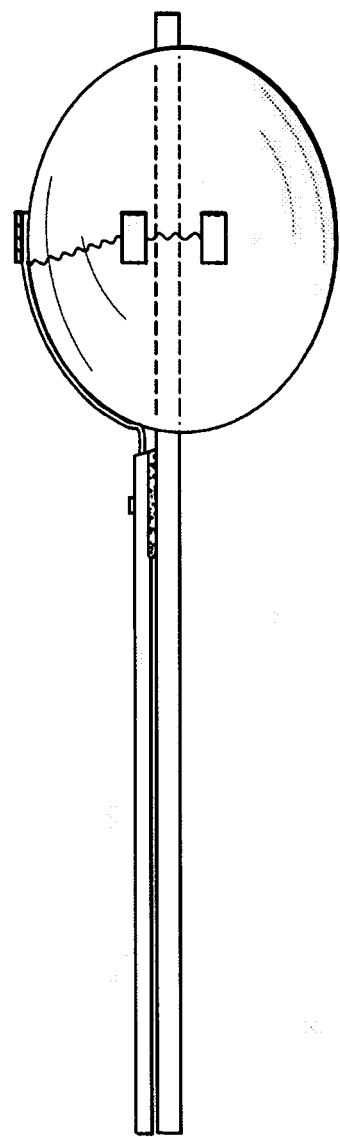

FIGS. 16A-16C illustrate an example method of applying an apparatus in a "T" configuration to an inflatable body.

As illustrated in FIG. 16A the array is applied while the balloon is fully deployed. An epoxy is applied to the catheter shaft, as close to the balloon as possible. The neck of the T-shaped configuration is applied down the shaft of the catheter so that the horizontal bar of the T lies around the equator of the balloon.

An adhesive can be applied to the force sensing elements array. As the force sensing elements array is separated from the balloon, a flexible bond adhesive can be applied, such as but not limited to a 208CTHF Ultra LightWeld (sold from DYMAX®, flexible bonding adhesive) to the backside of the "T". A small injector tip may be used to apply the adhesive. In an alternative example, DYMAX® bonding adhesive can be applied to the balloon.

As illustrated in FIG. 16B the sensing element array is placed on the balloon surface. The array is applied to the balloon, beginning near the shaft and working towards the equator. The arms of the "T" are wrapped around the balloon, making sure that the sensing elements are aligned around the equator and that the soluble tape is completely flat around the balloon.

The adhesive is cured. The DYMAX® adhesive is cured at about 630 mW/m$^2$. Each 5 mm$^2$ area can be exposed to UV light for about 15 seconds. In an alternative example, a low intensity UV chamber can be used for curing. The integrated system can be slowly rotated in the presence of the low UV light for about 30 seconds. Contact with the UV light source or the UV chamber should be avoided. After curing, the DYMAX® should be allowed to dry.

As illustrated in FIG. 16C the dissolvable tape can be dissolved. To dissolve the tape, the balloon can be placed in a water bath at room temperature. The integrated arrays-balloon system can be dried at room temperature.

An additional encapsulation layer can be applied, such as but not limited to a DYMAX® encapsulation layer. The encapsulation layer can be applied to cover the serpentine structures as well (including in the coupling bus and in the flexible interconnects). The force sensing elements pads may not be coated with an encapsulation layer.

The additional encapsulation layer may be cured.

FIG. 17 shows a schematic example of a balloon catheter including integrating sensing elements, such as capacitive-based force sensing elements, coupled with a data acquisition and graphical user interface. A data acquisition system is implemented to support the force sensing element to provide user feedback on the sensor sensitivity and speed. Once the force sensing element fabrication is completed, contact sensing is evaluated in a glass funnel apparatus to demonstrate feasibility. Taken together, the designs, fabrication strategies and feasibility measurements provide insight into the optimal configuration of conformal sensors on the inflatable body (such as but not limited to a balloon catheter). The data acquisition and user interface associated with the conformal sensing elements provide real time data on the behavior of different physicians and quantitative metrics on their occlusion technique. This information may be viewed as a function of time and show occlusion success rates as they relate to procedure outcomes.

In an example implementation, the data acquisition system for force-based contact sensing elements includes a National Instruments data acquisition system, a data acquisition (DAQ) hardware/software module for data acquisition, and calibration references. Measurements of the calibration references can be used to determine threshold values for analysis of the measurements, according to the principles described herein. The excitation current from the current source passes through tissue to generate a voltage, which may then be measured with a National Instruments PXI-6289 data acquisition card. LABVIEW® software (National Instruments Corporation, Austin, Tex.) can be used to control the output current and frequency of the excitation current. For the measurement, the measurements are taken at 1 kHz and 10 kHz. One function of the DAQ can be to display real-time contact data from the inflatable body in a manner that allows the user to interpret whether occlusion of the lumen has been achieved or not. In an example, a display separate from the data acquisition system can be used. To achieve a data acquisition system with a simple user-interface, binary (semi-quantitative) and quantitative (bar plots) representations of changes in force are used to facilitate visualization of an amount of contact across the sensors of an example system. In the binary representation, a baseline threshold is set based on the force detected when the balloon sensors are floating. A threshold for indicating if a force sensing element is in contact with the wall of the lumen is then set to a specific multiple of the baseline measurement.

Figure 18:
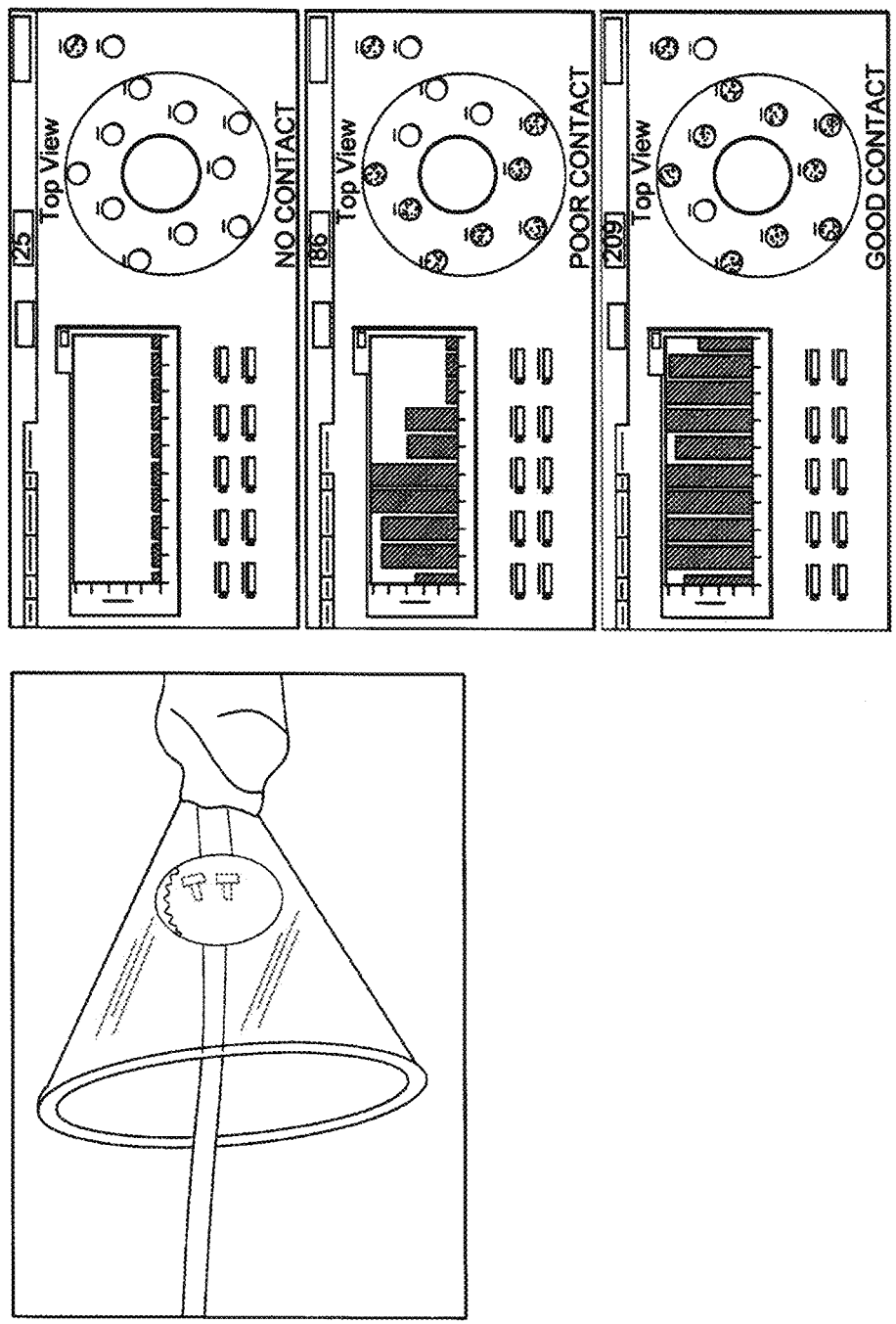
FIG. 18 provides a series of screen shots of an example graphical user interface demonstrating a variety of conditions simulated with a balloon catheter including integrated sensing electronics positioned in a glass heart, according to the principles described herein.

FIG. 18 provides a series of screen shots of a graphical user interface demonstrating a variety of conditions simulated with a balloon catheter including integrated sensing electronics positioned in a glass funnel.

The flex ribbon can be used to establish an interface with the force sensing elements and a data acquisition system. The conformal sensing elements can interface with an intermediate wires or flex ribbon in order to transmit data to a data acquisition system. To achieve this interconnection, flex ribbons can be used that have thin and narrow width profiles to transmit data along the slender catheter and out to the data acquisition system console. Custom bonding can be used to control pressure and temperature, set over a small range to achieve a robust electrically continuous interface. The devices can be routed along the shaft. Heat shrink can be used as insulation to shield the flex ribbon connections from the fluid environment inside the body.

A force can be measured upon insertion and inflation of the inflatable balloon (in this example, a cryoballoon) within a lumen. In the example of FIG. 18, the cavity of a glass funnel (~50 mm outer conical diameter) immersed in saline buffer solution (phosphate buffer solution) is used as a demonstration of a tissue lumen. The apparatus includes a thermal regulator/circulation unit to maintain body temperature in the bath. FIG. 18 shows representative data from conformal sensors nearby (no contact state) and in good contact with the funnel. The funnel test shows force values on the order of 10-15× greater during contact state relative to the force detected when the catheter is floating in saline. This initial study validated the concept of embedding contact sensors on the inflatable body (such as the cryoballoons).

The measurements of conformal sensors are provided to a data acquisition console to make measurements in an elastomeric phantom heart model. A catheter (n=7) in a phantom heart model can be deployed coupled with a 14 F sheath access port. This initial study is used as a way to evaluate encapsulation polymers and durability of the conformal sensors on the balloon. Initial results with UV-curable polymer adhesives showed significant delamination upon entry into the phantom left atrium. With usage, some delaminations of the serpentine buses and contact sensor pads may occur. In various examples, different types of polyurethane encapsulants can be used to enhance the mechanical stability of the serpentine buses and contact sensor pads, promoting greater durability while preserving stretchability, transparency, and biocompatibility.

Use of an encapsulant according to the principles herein, in addition to enhancing delamination, reduced the thermal effects of having conformal sensors on the balloon during cryoablation and minimized the effect of cryo-thermal cycling on performance of the force sensing elements. The results demonstrated minimal changes in thermocouple measurements for cryoballoons with embedded sensors relative to those without, indicating that the conformal sensors minimally act as thermal sinks Cryothermal cycling is conducted using an alcohol bath adjusted to −56° C. Cryoballoons with conformal sensors exposed to this temperature over many cycles at 4-minute intervals. No changes are seen in sensor optical characteristics and overall performance following this testing. These results indicate that repeated exposure to cryoenergy does not affect the performance of conformal sensors on the cryoballoon. Other catheter features, including mechanical deflection, sheath deployment and shaft size, are all examined to understand the impact of contact sensors on the overall look/feel and performance of the cryoballoon with embedded contact sensors.

To establish a robust quantitative means of assessing occlusion, the changes in force measured during cryoballoon occlusion in the right superior PV (RSPV) can be assessed. The results provide, for the first time, a new way to assess occlusion while concurrently allowing the collection of new data on the behavior and successes of individual cryoballoon operators. These behaviors are evaluated during occlusion prior to ablation and during cryoenergy injection.

The cryoballoon contact is measured using capacitive-base force sensing in a tissue lumen of live pigs by deploying inflatable bodies with contact sensors through a 14 F sheath into the left atrium. Tests show sensors can assess contact with PV ostium immediately prior to cryoablation.

Figure 19:
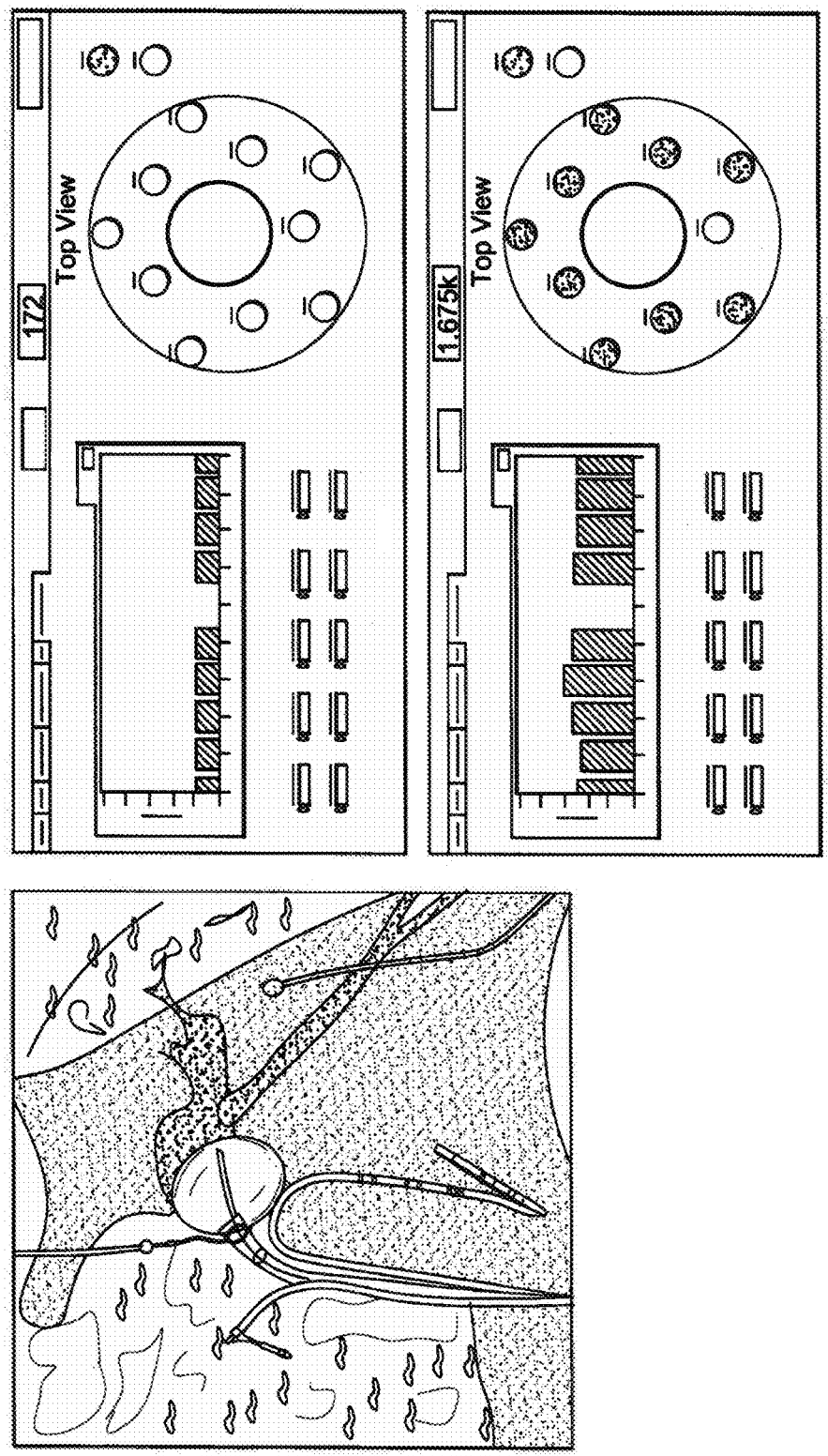
FIG. 19 provides a series of screen shots of an example graphical user interface demonstrating a variety of contact conditions with a balloon catheter including integrated sensing electronics positioned in a tissue lumen of a live pig, according to the principles described herein.

FIG. 19 provides a series of screen shots of a graphical user interface demonstrating a variety of contact conditions with a balloon catheter including integrated sensing electronics positioned in a tissue lumen of a live pig.

FIG. 19 also shows results from a left superior pulmonary vein of a pig heart whereby contact is achieved across all active sensors and confirmed with injection of contrast dye. These measurements are reproducible across two different pig measurements and across multiple trials runs in each animal.

FIG. 19 further demonstrates an example user interface displaying binary read outs of sensors disposed on a balloon catheter. In the example of FIG. 19, each circle corresponds to a sensing element, and provides a representation of a state of the force sensing element. In this example, an open circle on the display corresponds to no contact between a sensing element and the tissue, and the shaded circle indicates an amount of contact between a sensing element and the tissue.

Figure 20A:
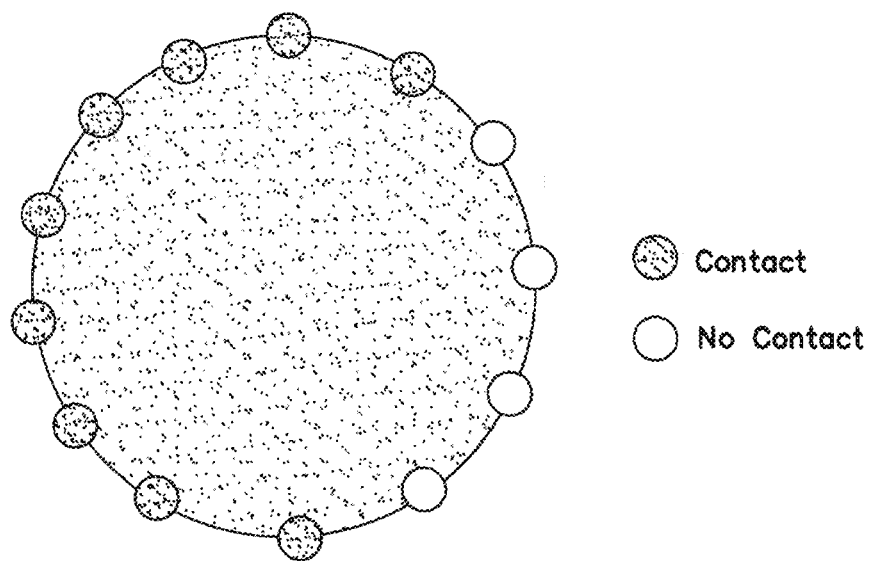
FIGS. 20A and 20B illustrate example visualizations of contact sensing from measured data, according to the principles described herein.
Figure 20B:
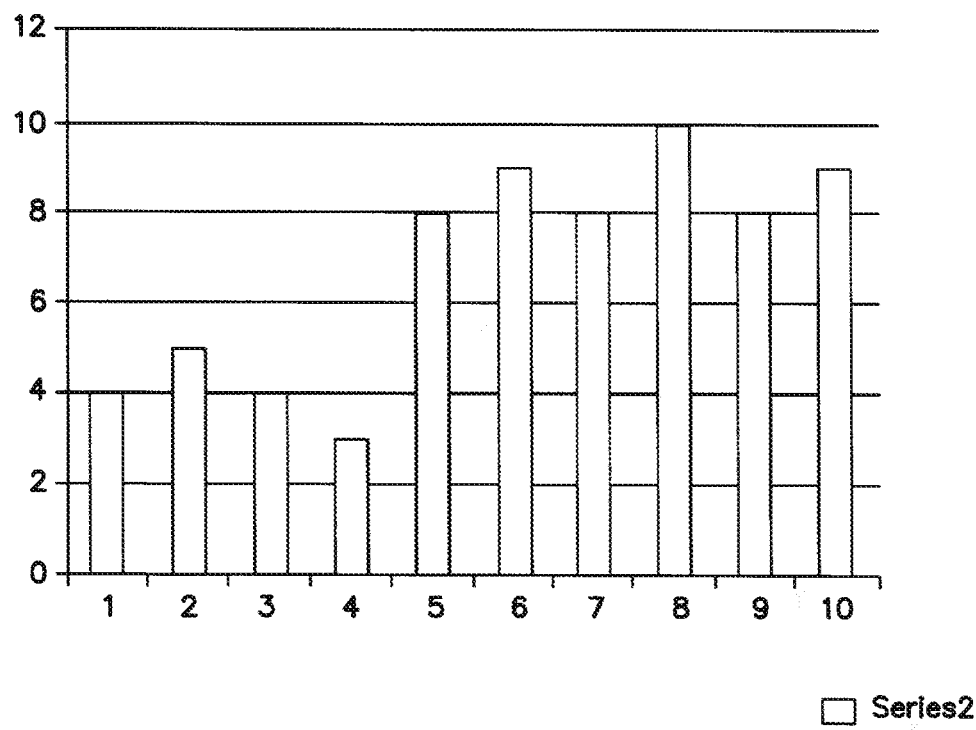

FIGS. 20A and 20B illustrate another example of a visualization for contact sensing from measured data. Such visualization can help personnel in making assessments on occlusion. Specifically, FIG. 20A is a simplified representation of the balloon cross section. Through color or texture of the small circles representing each sensor, the example user interface can be used to indicate whether a sufficient contact force is experienced by a given sensing element. For example, a measured value of the force sensing element above a threshold value can be decided as an indicator that the sensor has established contact with a portion of tissue, a measured value of the force sensing element below the threshold value can be decided as an indicator that the sensor has not established contact with a portion of tissue. FIG. 20B is an example chart representation of a measure of contact force experienced by each sensor.

While the user interface of FIGS. 19, 20A and 20B are described in terms of indication of contact force between the force sensing elements and the tissue, the user interface and visualization technique can be applied to display the results of other measurements, including impedance, temperature, pressure, or any other type of measurement that sensing elements according to the principles herein can be used to measure.

Figure 21:
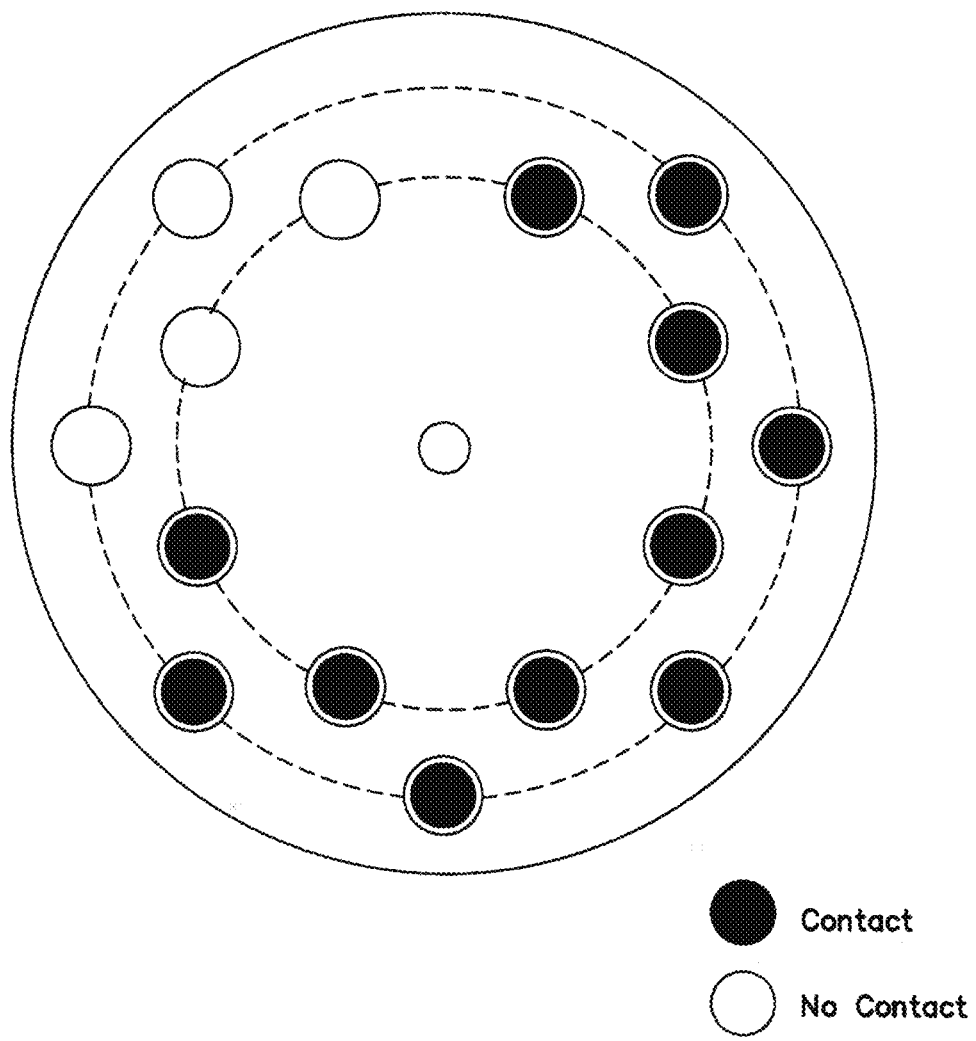
FIG. 21 demonstrates another example user interface displaying binary read outs of sensors disposed on a balloon catheter, according to the principles described herein.

FIG. 21 demonstrates another example user interface displaying binary read outs of sensing elements disposed on an inflatable body (here a balloon catheter). In this example, an open circle on the display corresponds to no contact between a sensing element and the tissue, and the shaded circle indicates an amount of contact between a sensing element and the tissue.

Figure 22:
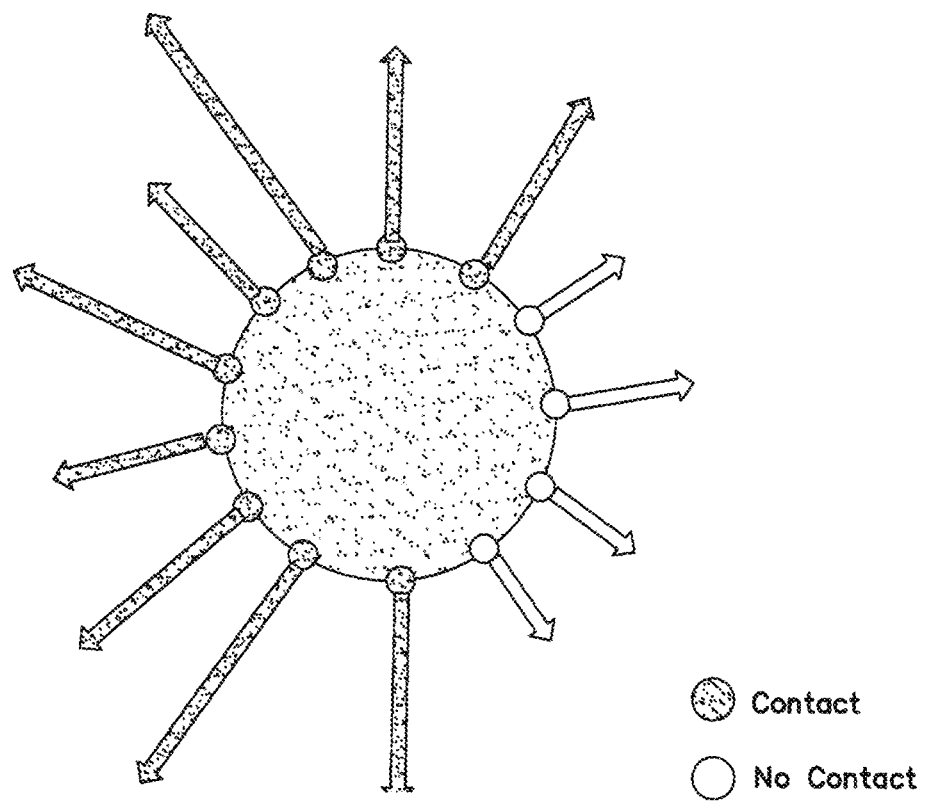
FIG. 22 demonstrates an example user interface displaying quantitative read outs of sensors disposed on a balloon catheter, according to the principles described herein.
Figure 23:
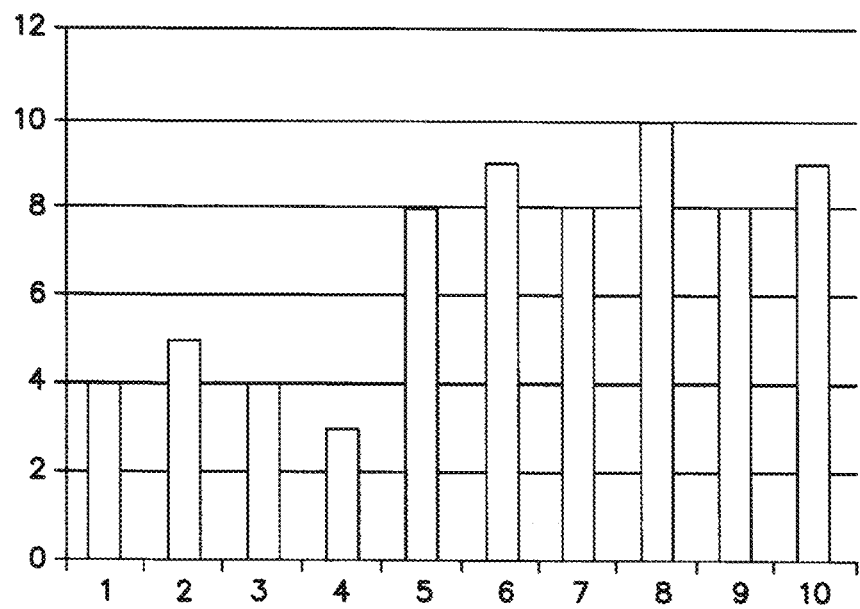
FIG. 23 demonstrates an another example user interface displaying quantitative read outs of sensors disposed on a balloon catheter, according to the principles described herein.

FIG. 22 demonstrates an example user interface displaying quantitative read outs of sensing elements disposed on an inflatable body (here a balloon catheter). In this example, a length of an arrow at each sensing element representation serves as an indicator of the amount of a measurement from the respective sensing element. The amount of the measurement is quantitatively shown in the bar graph chart of FIG. 23.

Figure 24:
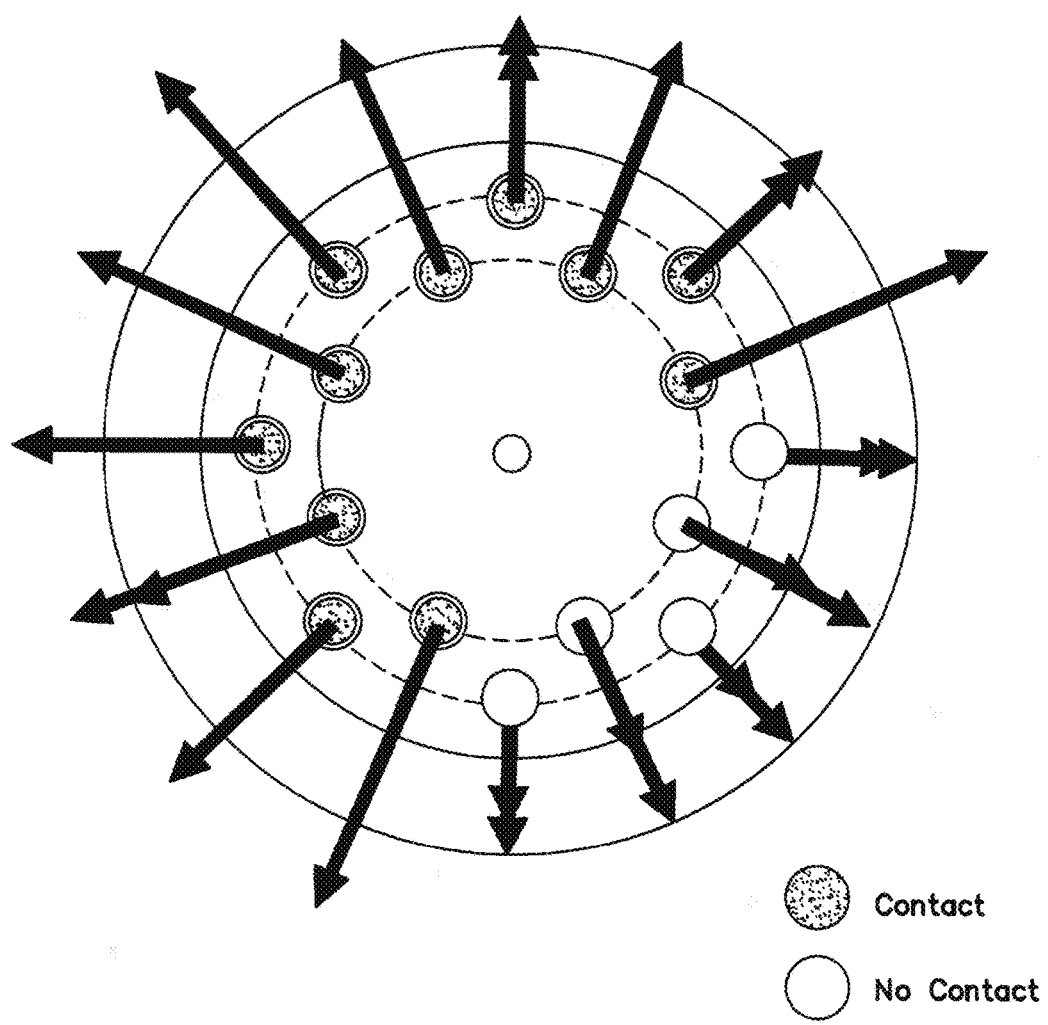
FIG. 24 demonstrates another example user interface displaying quantitative read outs of sensors disposed on a balloon catheter, according to the principles described herein.

FIG. 24 demonstrates another example user interface displaying quantitative read outs of sensors disposed on a balloon catheter. In this example, the sensor representations are arranged in two different diameter circles, which can be used to indicate the spatial distribution of the force sensing elements on the inflatable body. For example, the force sensing element representations in the smaller circle can be used to indicate measurements of sensing elements disposed closer to a top portion of the inflatable body; the force sensing element representations in the larger circle can be used to indicate measurements of sensing elements disposed farther from the top portion of the inflatable body. In this example, a length of an arrow at each sensing element representation serves as an indicator of the amount of a measurement from the respective sensing element. A measurement below a threshold value can be classified as no contact, while a measurement above the threshold value indicates an amount of contact.

Figure 25C:
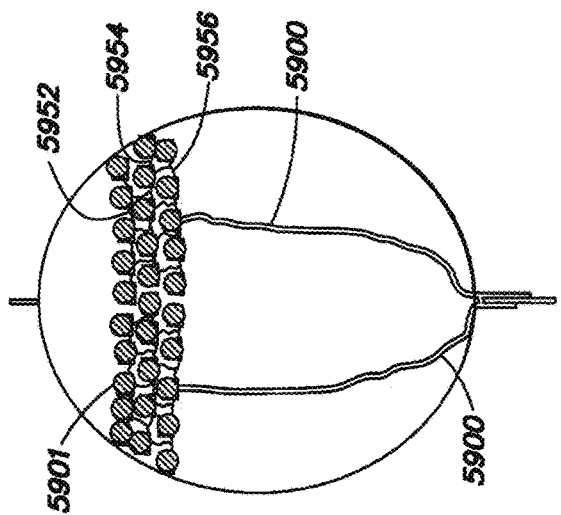
FIGS. 25A-25C illustrates additional examples of the sensor configuration on the balloon surface, according to the principles described herein.
Figure 25B:
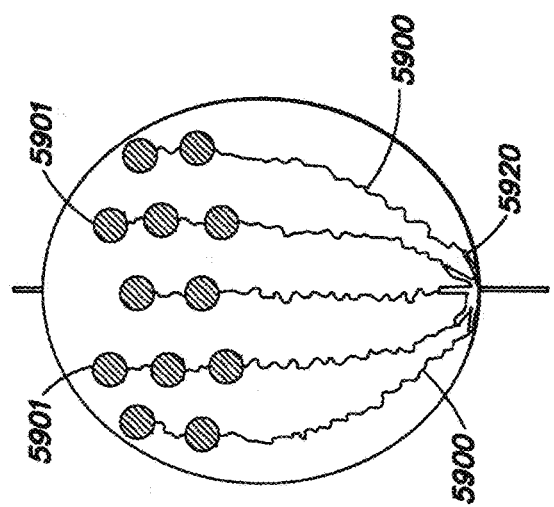
Figure 25A:
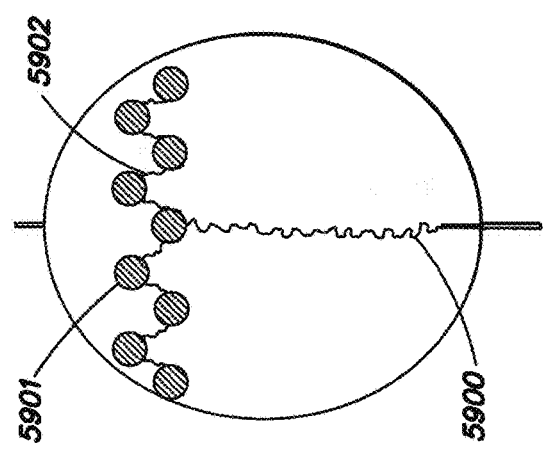

FIGS. 25A-25C illustrates additional examples of force sensing elements configurations on the balloon surface, according to the principles described herein. Multiple independent flex boards can be used to increase the total number of sensors. For example, FIGS. 25A-25C illustrate that the flexible interconnects 5900 leading from the force sensing elements 5901 can be routed down towards the base of the inflatable body. FIG. 25A shows the force sensing elements 5901 can be disposed along two different latitudes of the inflatable body, and the coupling bus 5902 can run sequentially from a sensing element at one latitude to a sensing element in another latitude. FIG. 25B shows that the flexible interconnect 5900 can be routed down towards the base of the inflatable body where a coupling bus 5920 may be located. FIG. 25C shows an example that includes more than one coupling bus. In this example, there are three coupling buses 5952, 5954, 5956, each associated with a different latitude of the inflatable body. In this example, the force sensing elements 5901 are disposed along each of the three different latitudes of the inflatable body, and the force sensing elements 5901 along each latitude are connected with a respective coupling bus.

FIGS. 26A-26B illustrate additional configurations of the force sensing elements array, including "L" shaped arrays, according to the principles herein. For example, FIGS. 26A-26B illustrate that the flexible interconnects 6000 leading from the force sensing elements 6001 can be routed down towards the base of the inflatable body. FIG. 26A shows that the force sensing elements 6001 can be disposed along two different latitudes of the inflatable body, and the coupling bus 6002 can run between the two latitudes, with other flexible interconnects 6004. FIG. 26B shows that the force sensing elements 6001 can be disposed along two different latitudes of the inflatable body, and each latitude can have a respective coupling bus 6010 and 6012, with a different flexible interconnect running to each respective coupling bus 6010 or 6012.

Figure 27A:
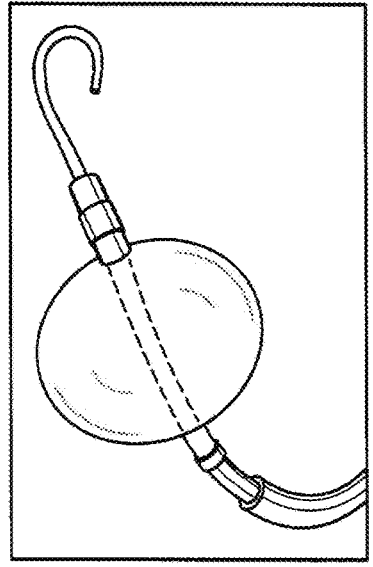
FIGS. 27A-27C illustrates examples of balloon catheter devices, according to the principles described herein.
Figure 27B:
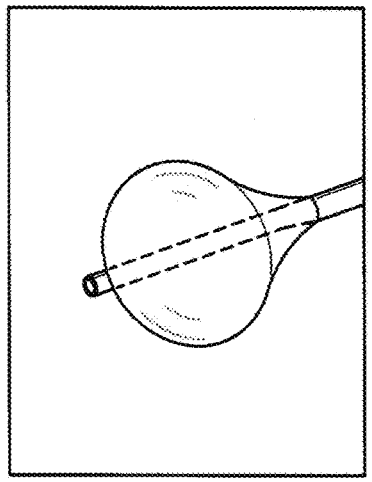
Figure 27C:
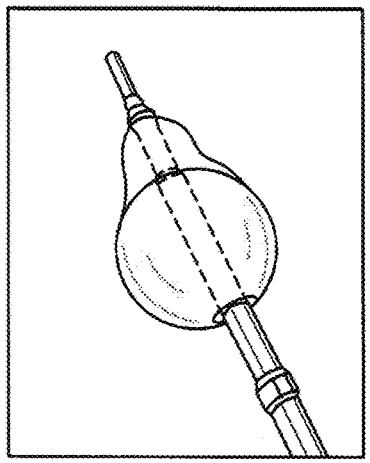

FIGS. 27A-27C illustrate examples of multi-sensing element devices and catheter devices. FIGS. 27A-27C show the balloon-based ablation catheters that can be used to apply cryo-, laser-, and high intensity ultrasound-forms of therapy when deployed proximate to tissue. Any stretchable electronic system according to the principles described herein can be disposed on any of the inflatable bodies of the catheters shown in FIGS. 27A-27C.

A configuration of stretchable electronic system according to the principles herein can be disposed on the surface of any of these example devises according to the principles herein. The description herein concerning determining the areas of minimal curvature of the inflatable body when in the deflated state can be applied to any of the example devices of FIGS. 27A-27C in going from a fully deployed state to a collapsed state (that has dimensions smaller than the fully deployed state), including the netting shape surface.

In various examples disclosed herein, therapeutic apparatus are configured in the ways described herein to provide ablative therapy, which may comprise an element capable of emitting various forms of electromagnetic radiation including microwave energy, thermal energy, laser, or radio frequency (RF) electromagnetic (EM) radiation.

In other examples, the element comprises an ultrasound emitter for ultrasonic ablation. In such examples, the therapeutic facility (or element thereof) comprises an array of ultrasound transducers (e.g. piezoelectric crystals). Each island comprises a receiver that senses acoustic reflections generated by a source emitter that sends acoustic waves through the tissue at megahertz frequencies.

In still other examples, the device is configured to provide cryo-ablation. Further, by coupling delivery channels and micro-valves to the selectively operative circuitry in the manners described herein, cryo-ablation may be delivered by the therapeutic facility or selected portions thereof.

In ablative examples, the substrate may be stretchable as disclosed above and herein and provided with the stretchable circuitry described herein. Also as described herein, the stretchable circuitry is able to remain functional upon conforming to the surface of the tissue, which in examples for ablation, would comprise conformal contact with some surface of the heart or cardiovascular system, including the ostium of a pulmonary vein, any surface of a vein or artery, a septal wall of the heart, an atrial surface of a heart, or a ventricular surface of a heart.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While various inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described examples can be implemented in any of numerous ways. For example, some examples may be implemented using hardware, software or a combination thereof. When any aspect of an example is implemented at least in part in software, the software code can be executed on any suitable processor or collection of processors, whether provided in a single computer or distributed among multiple computers.

In this respect, various aspects may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various examples of the technology described above. The computer readable medium or media can be transportable, such that the program or programs stored thereon can be loaded onto one or more different computers or other processors to implement various aspects of the present technology as described above.

The terms "program" or "software" are used herein in a generic sense to refer to any type of computer code or set of computer-executable instructions that can be employed to program a computer or other processor to implement various aspects of the present technology as described above. Additionally, it should be appreciated that according to one aspect of this example, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various examples.

Also, the technology described herein may be embodied as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one example, to A only (optionally including elements other than B); in another example, to B only (optionally including elements other than A); in yet another example, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one example, to at least one, optionally including more than one, A, with no B present (and optionally including elements other than B); in another example, to at least one, optionally including more than one, B, with no A present (and optionally including elements other than A);

in yet another example, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All examples that come within the spirit and scope of the following claims and equivalents thereto are claimed.

The invention claimed is:

1. An apparatus for medical diagnosis and/or treatment, the apparatus comprising:
    a flexible substrate forming an inflatable body; and
    a plurality of force sensing elements disposed on the flexible substrate, each force sensing element of the plurality of force sensing elements comprising:
        first and second conductive components and an elastic dielectric component in a stacked arrangement on the flexible substrate, the first conductive component being stacked between the second conductive component and the flexible substrate, and
        the elastic dielectric component being stacked between the first and second conductive components,
    wherein a measure of an electrical property of at least one of the first and second conductive components provides an indication of a force applied to the inflatable body.

2. An apparatus for medical diagnosis and/or treatment, the apparatus comprising:
    a flexible substrate forming an inflatable body; and
    a coupling bus disposed on the flexible substrate about a portion of a circumference of the inflatable body;
    a plurality of force sensing element disposed on the flexible substrate, each force sensing element of the plurality of force sensing elements comprising:
        first and second conductive components and an elastic dielectric component in a stacked arrangement on the flexible substrate, the first conductive component being stacked between the second conductive component and the flexible substrate, and
        the elastic dielectric component being stacked between the first and the second conductive components,
    wherein each of the plurality of force sensing elements is coupled to the coupling bus, and a measure of an electrical property of at least one of the first and second conductive components provides an indication of a force applied to the inflatable body.

3. The apparatus of claim 2, wherein the coupling bus is a serpentine bus, and wherein the serpentine bus electrically couples at least one conductive component of each of the plurality of force sensing elements.

4. The apparatus of claim 2, further comprising an encapsulation material disposed over substantially a portion of the coupling bus.

5. The apparatus of claim 4, wherein the encapsulation material comprises polyurethane.

6. The apparatus of claim 1 or 2, further comprising a shaft coupled to the inflatable body, wherein the shaft comprises a cryoablation device, a laser ablation device, a high intensity ultrasound or a RF device.

7. The apparatus of claim 2, wherein the coupling bus is an annular bus, and wherein the annular bus is disposed as a ring substantially about a circumference of the inflatable body.

8. The apparatus of claim 2, wherein the coupling bus is a serpentine bus, and wherein the serpentine bus comprises a plurality of serpentine structures.

9. The apparatus of claim 1 or 2, wherein the plurality of force sensing elements is disposed about an equator of the inflatable body.

10. The apparatus of claim 1 or 2, wherein the plurality of force sensing elements is disposed proximate to a distal portion of the inflatable body.

11. The apparatus of claim 1 or 2, wherein the plurality of force sensing elements is disposed in a helical pattern about the inflatable body.

12. The apparatus of claim 1 or 2, wherein the inflatable body is disposed near a distal end of a catheter.

13. The apparatus of claim 1 or 2, wherein the inflatable body is a balloon.

14. The apparatus of claim 13, wherein the balloon is cylindrical, onion-shaped, cone-shaped, dog-bone-shaped, barrel-shaped.

15. The apparatus of claim 2, wherein the coupling bus has a T-configuration or an annular ring structure.

16. The apparatus of claim 1 or 2, wherein the force applied to the inflatable body causes a degree of compression of the elastic dielectric component between the first and second conductive components, and wherein the measure of the electrical property of the at least one of the first and second conductive components changes based on the degree of compression of the elastic dielectric component, thereby providing an indication of the force applied to the inflatable body.

17. The apparatus of claim 1 or 2, wherein each force sensing element of the plurality of force sensing elements is formed from a conductive material.

18. The apparatus of claim 1 or 2, wherein, for at least one force sensing element of the plurality of force sensing elements, one of the first and second conductive components is larger than another of the first and second conductive components.

* * * * *